United States Patent
Hincapie Ordonez et al.

(10) Patent No.: US 9,089,267 B2
(45) Date of Patent: Jul. 28, 2015

(54) METHODS AND APPARATUS FOR ADJUSTING NEUROSTIMULATION INTENSITY USING EVOKED RESPONSES

(75) Inventors: Juan Gabriel Hincapie Ordonez, Maple Grove, MN (US); David J. Ternes, Roseville, MN (US); Jason J. Hamann, Blaine, MN (US); Stephen Ruble, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 384 days.

(21) Appl. No.: 13/156,914

(22) Filed: Jun. 9, 2011

(65) Prior Publication Data

US 2011/0313495 A1     Dec. 22, 2011

Related U.S. Application Data

(60) Provisional application No. 61/356,251, filed on Jun. 18, 2010.

(51) Int. Cl.
  *A61N 1/36* (2006.01)
  *A61B 5/04* (2006.01)
  *A61B 5/00* (2006.01)

(52) U.S. Cl.
  CPC ........ *A61B 5/04001* (2013.01); *A61N 1/36053* (2013.01); *A61N 1/36114* (2013.01); *A61N 1/36117* (2013.01); *A61N 1/36128* (2013.01); *A61N 1/36135* (2013.01); *A61N 1/36139* (2013.01); *A61B 5/4041* (2013.01)

(58) Field of Classification Search
  CPC ........... A61N 1/36114; A61N 1/36117; A61N 1/36128; A61N 1/36135; A61N 1/36139
  USPC .......................................... 607/2, 17, 18, 62
  See application file for complete search history.

(56) References Cited

U.S. PATENT DOCUMENTS

| 4,934,366 A | 6/1990 | Truex et al. |
| 4,940,052 A | 7/1990 | Mann et al. |
| 6,104,956 A | 8/2000 | Naritoku et al. |
| 6,192,275 B1 | 2/2001 | Zhu et al. |

(Continued)

FOREIGN PATENT DOCUMENTS

| AU | 2011267992 B2 | 10/2013 |
| CN | 103079636 A | 5/2013 |

(Continued)

OTHER PUBLICATIONS

Braund, K. G, et al., "Morphologic and morphometric studies of the vagus and recurrent laryngeal nerves in clinically normal adult dogs", Am J Vet Res., 49(12), (Dec. 1988), 2111-6.

(Continued)

*Primary Examiner* — Niketa Patel
*Assistant Examiner* — William Levicky
(74) *Attorney, Agent, or Firm* — Schwegman Lundberg & Woessner, P.A.

(57) ABSTRACT

A neurostimulation system provides for capture verification and stimulation intensity adjustment to ensure effectiveness of vagus nerve stimulation in modulating one or more target functions in a patient. In various embodiments, stimulation is applied to the vagus nerve, and evoked responses are detected to verify that the stimulation captures the vagus nerve and to adjust one or more stimulation parameters that control the stimulation intensity.

11 Claims, 19 Drawing Sheets

(56) References Cited

U.S. PATENT DOCUMENTS

| | | | |
|---|---|---|---|
| 6,466,822 | B1 | 10/2002 | Pless |
| 6,556,868 | B2 | 4/2003 | Naritoku et al. |
| 7,134,994 | B2 | 11/2006 | Alpert et al. |
| 7,720,548 | B2 * | 5/2010 | King ............................ 607/62 |
| 8,031,076 | B2 | 10/2011 | Sachanandani et al. |
| 2002/0072776 | A1 | 6/2002 | Osorio et al. |
| 2004/0054297 | A1 | 3/2004 | Wingeier et al. |
| 2005/0033189 | A1 | 2/2005 | Mccraty et al. |
| 2005/0131476 | A1 | 6/2005 | Kim et al. |
| 2005/0137645 | A1 | 6/2005 | Voipio et al. |
| 2006/0106428 | A1 | 5/2006 | Libbus et al. |
| 2006/0135998 | A1 * | 6/2006 | Libbus et al. .................... 607/2 |
| 2006/0167497 | A1 | 7/2006 | Armstrong et al. |
| 2006/0224198 | A1 * | 10/2006 | Dong et al. ....................... 607/9 |
| 2006/0241725 | A1 | 10/2006 | Libbus |
| 2007/0179557 | A1 | 8/2007 | Maschino et al. |
| 2007/0219593 | A1 | 9/2007 | Yonce et al. |
| 2008/0021504 | A1 | 1/2008 | McCabe et al. |
| 2008/0058873 | A1 | 3/2008 | Lee et al. |
| 2008/0058874 | A1 * | 3/2008 | Westlund et al. ................. 607/2 |
| 2008/0058892 | A1 | 3/2008 | Haefner et al. |
| 2008/0103532 | A1 | 5/2008 | Armstrong et al. |
| 2008/0161651 | A1 | 7/2008 | Peterson et al. |
| 2008/0300655 | A1 | 12/2008 | Cholette |
| 2009/0024186 | A1 * | 1/2009 | Brockway et al. ............. 607/59 |
| 2009/0036950 | A1 * | 2/2009 | Armstrong et al. ............. 607/45 |
| 2009/0299421 | A1 | 12/2009 | Sawchuk |
| 2010/0010556 | A1 | 1/2010 | Zhao et al. |
| 2010/0114217 | A1 * | 5/2010 | Krause et al. ..................... 607/5 |
| 2010/0191311 | A1 | 7/2010 | Scheiner et al. |
| 2011/0313483 | A1 | 12/2011 | Hincapie Ordonez et al. |
| 2011/0313484 | A1 | 12/2011 | Hincapie Ordonez et al. |

FOREIGN PATENT DOCUMENTS

| | | | |
|---|---|---|---|
| EP | 20060241725 | A1 | 10/2006 |
| JP | 2008520353 | A | 6/2008 |
| JP | 2008538996 | A | 11/2008 |
| JP | 2010502275 | A | 1/2010 |
| WO | WO-2011159545 | A2 | 12/2011 |
| WO | WO-2011159545 | A3 | 12/2011 |

OTHER PUBLICATIONS

Hursh, J. B, et al., "Conduction velocity and diameter of nerve fibers.", American Journal of Physiology, 127, (1939), 131-139.

Koo, B., et al., "Human vagus nerve electrophysiology: a guide to vagus nerve stimulation parameters", J Clin Neurophysiol., 18(5), (Sep. 2001), 429-33.

Smith, C. D, et al., "The Chronaxie and Propagation Velocity of Canine Cervical Vagus Nerve Fibers In Vivo", Cardiovascular Engineering, 1(2), (Jun. 2001), 77-84.

"U.S. Appl. No. 13/156,879 , Response filed Jul. 23, 2013 to Non Final Office Action mailed Mar. 26, 2013", 11 pgs.

"U.S. Appl. No. 13/156,879, Non Final Office Action mailed Mar. 26, 2013", 15 pgs.

"U.S. Appl. No. 13/156,891, Non Final Office Action mailed Apr. 17, 2013", 16 pgs.

"U.S. Appl. No. 13/156,891, Response filed Jul. 16, 2013 to Non Final Office Action mailed Apr. 17, 2013", 11 pgs.

"International Application Serial No. PCT/US2011/039764, International Preliminary Report on Patentability mailed Jan. 3, 2013", 15 pgs.

"International Application Serial No. PCT/US2011/039764, Invitation to Pay Additional Fees mailed Sep. 21, 2011", 8 pgs.

"International Application Serial No. PCT/US2011/039764, Search Report mailed Jan. 31, 2012", 6 pgs.

"International Application Serial No. PCT/US2011039764, Written Opinion mailed Jan. 31, 2012", 13 pgs.

"U.S. Appl. No. 13/156,879, Advisory Action mailed Oct. 25, 2013", 5 pgs.

"U.S. Appl. No. 13/156,879, Appeal Brief filed Jan. 13, 2014", 21 pgs.

"U.S. Appl. No. 13/156,879, Final Office Action mailed Aug. 15, 2013", 16 pgs.

"U.S. Appl. No. 13/156,879, Non Final Office Action mailed Jul. 8, 2014", 15 pgs.

"U.S. Appl. No. 13/156,879, Notice of Allowance mailed Feb. 14, 2014", 7 pgs.

"U.S. Appl. No. 13/156,879, Notice of Allowance mailed Oct. 21, 2014", 7 pgs.

"U.S. Appl. No. 13/156,879, Response filed Sep. 30, 2014 to Non Final Office Action mailed Jul. 8, 2014", 11 pgs.

"U.S. Appl. No. 13/156,879, Response filed Oct. 8, 2013 to Final Office Action mailed Aug. 15, 2013", 12 pgs.

"U.S. Appl. No. 13/156,891, Advisory Action mailed Oct. 25, 2013", 5 pgs.

"U.S. Appl. No. 13/156,891, Final Office Action mailed Aug. 19, 2013", 17 pgs.

"U.S. Appl. No. 13/156,891, Non Final Office Action mailed Aug. 26, 2014", 20 pgs.

"U.S. Appl. No. 13/156,891, Response filed Oct. 8, 2013 to Final Office Action mailed Aug. 19, 2013", 10 pgs.

"U.S. Appl. No. 13/156,891, Response filed Nov. 12, 2014 to Non Final Office Action mailed Aug. 26, 2014", 10 pgs.

"Chinese Application Serial No. 201180039980.0, Office Action mailed May 14, 2014", With English Translation, 26 pgs.

"Chinese Application Serial No. 201180039980.0, Office Action mailed Oct. 24, 2014", 11 pgs.

"European Application Serial No. 11726611.4, Office Action mailed Oct. 28, 2013", 7 pgs.

"Japanese Application Serial No. 2013515389, Office Action mailed Sep. 8, 2014", With Partial Translation, 4 pgs.

\* cited by examiner

METHODS AND APPARATUS FOR ADJUSTING NEUROSTIMULATION INTENSITY USING EVOKED RESPONSES

CLAIM OF PRIORITY

This application claims the benefit of priority under 35 U.S.C. §119(e) of U.S. Provisional Patent Application Ser. No. 61/356,251, filed on Jun. 18, 2010, which is herein incorporated by reference in its entirety.

CROSS REFERENCE TO RELATED APPLICATIONS

The following commonly assigned U.S. patent applications are related, and are herein incorporated by reference in their entirety: "METHODS AND APPARATUS FOR CONTROLLING NEUROSTIMULATION USING EVOKED NEURAL RESPONSES," Ser. No. 13/156,879, filed on Jun. 9, 2011, published as U.S. 2011/0313483, and "METHODS AND APPARATUS FOR CONTROLLING NEUROSTIMULATION USING EVOKED PHYSIOLOGIC EVENTS," Ser. No. 13/156,891, filed on Jun. 9, 2011, published as U.S. 2011/0313484.

TECHNICAL FIELD

This document relates generally to neurostimulation and more particularly to a neurostimulation system that detects evoked responses and uses the detected evoked responses for capture verification and parameter adjustment.

BACKGROUND

Vagus nerve stimulation has been applied to modulate various physiologic functions and treat various diseases. One example is the modulation of cardiac functions in a patient suffering heart failure or myocardial infarction. The myocardium is innervated with sympathetic and parasympathetic nerves including the cardiac branches of the vagus nerve. Activities in the vagus nerve, including artificially applied electrical stimuli, modulate the heart rate and contractility (strength of the myocardial contractions). Electrical stimulation applied to the vagus nerve is known to decrease the heart rate and the contractility, lengthening the systolic phase of a cardiac cycle, and shortening the diastolic phase of the cardiac cycle. This ability of vagus nerve stimulation is utilized, for example, to control myocardial remodeling.

In addition to treating cardiac disorders such as myocardial remodeling, vagus nerve stimulation is also known to be effective in treating disorders including, but not limited to, depression, anorexia nervosa/eating disorders, pancreatic function, epilepsy, hypertension, inflammatory disease, and diabetes. To ensure efficacy of a vagus nerve stimulation therapy, there is a need to verify that the stimulation activates the target branches of the vagus nerve and control the stimulation parameters to result in effective modulation of target functions.

SUMMARY

A neurostimulation system provides for capture verification and stimulation intensity adjustment to ensure effectiveness of vagus nerve stimulation in modulating one or more target functions in a patient. In various embodiments, stimulation is applied to the vagus nerve, and evoked responses are detected to verify that the stimulation captures the vagus nerve and to adjust one or more stimulation parameters that control the stimulation intensity.

In one embodiment, a system for delivering neurostimulation includes a stimulation output circuit, an evoked response detection circuit, and a control circuit. The stimulation output circuit delivers neurostimulation pulses to a vagus nerve. The evoked response detection circuit receives a physiological signal indicative of evoked responses being physiologic events evoked by the neurostimulation pulses and detects the evoked muscular responses using the physiological signal. The control circuit controls the delivery of the neurostimulation pulses using a stimulation intensity and includes a stimulation parameter adjustor and a stimulation adjustment timer. The stimulation parameter adjustor adjusts the stimulation intensity using the detected evoked responses. The stimulation adjustment timer times the adjustment of the stimulation intensity using the detected evoked responses according to a specified schedule.

In one embodiment, a method for delivering neurostimulation is provided. Neurostimulation pulses are delivered to the vagus nerve. The delivery of the neurostimulation pulses is controlled using a stimulation intensity. Levels of the stimulation intensity are swept at specified increments. A physiological signal indicative of evoked responses is sensed. The evoked responses are each a physiologic event evoked by one of the neurostimulation pulses. The evoked responses are detected using the physiological signal. A stimulation threshold is determined. The stimulation intensity is a minimum level of the stimulation intensity for providing one or more specified characteristics of the evoked responses. The stimulation intensity is adjusted for modulating a specified physiologic function using the stimulation threshold.

In one embodiment, a system for delivering neurostimulation includes a stimulation output circuit, an evoked response detection circuit, and a control circuit. The stimulation output circuit delivers neurostimulation pulses to a vagus nerve. The evoked response detection circuit receives a physiological signal indicative of evoked responses being physiologic events evoked by the neurostimulation pulses and detects one of the evoked muscular responses for each pulse of the neurostimulation pulses delivered using the physiological signal. The control circuit controls the delivery of the neurostimulation pulses using a stimulation intensity. The control circuit includes a stimulation parameter adjustor that adjusts the stimulation intensity in response to a specified number of the evoked neural responses not detected for a specified number of the neurostimulation pulses delivered.

In one embodiment, a method for delivering neurostimulation is provided. Neurostimulation pulses are delivered to the vagus nerve. The delivery of the neurostimulation is controlled using a stimulation intensity. A capture verification is performed. The capture verification includes sensing a physiological signal indicative of evoked responses each being a physiologic event evoked by one of the neurostimulation pulses, detecting one of the evoked responses for each pulse of the neurostimulation pulses delivered, and adjusting the stimulation intensity in response to a specified number of the evoked responses not detected for a specified number of the neurostimulation pulses delivered.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof.

The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
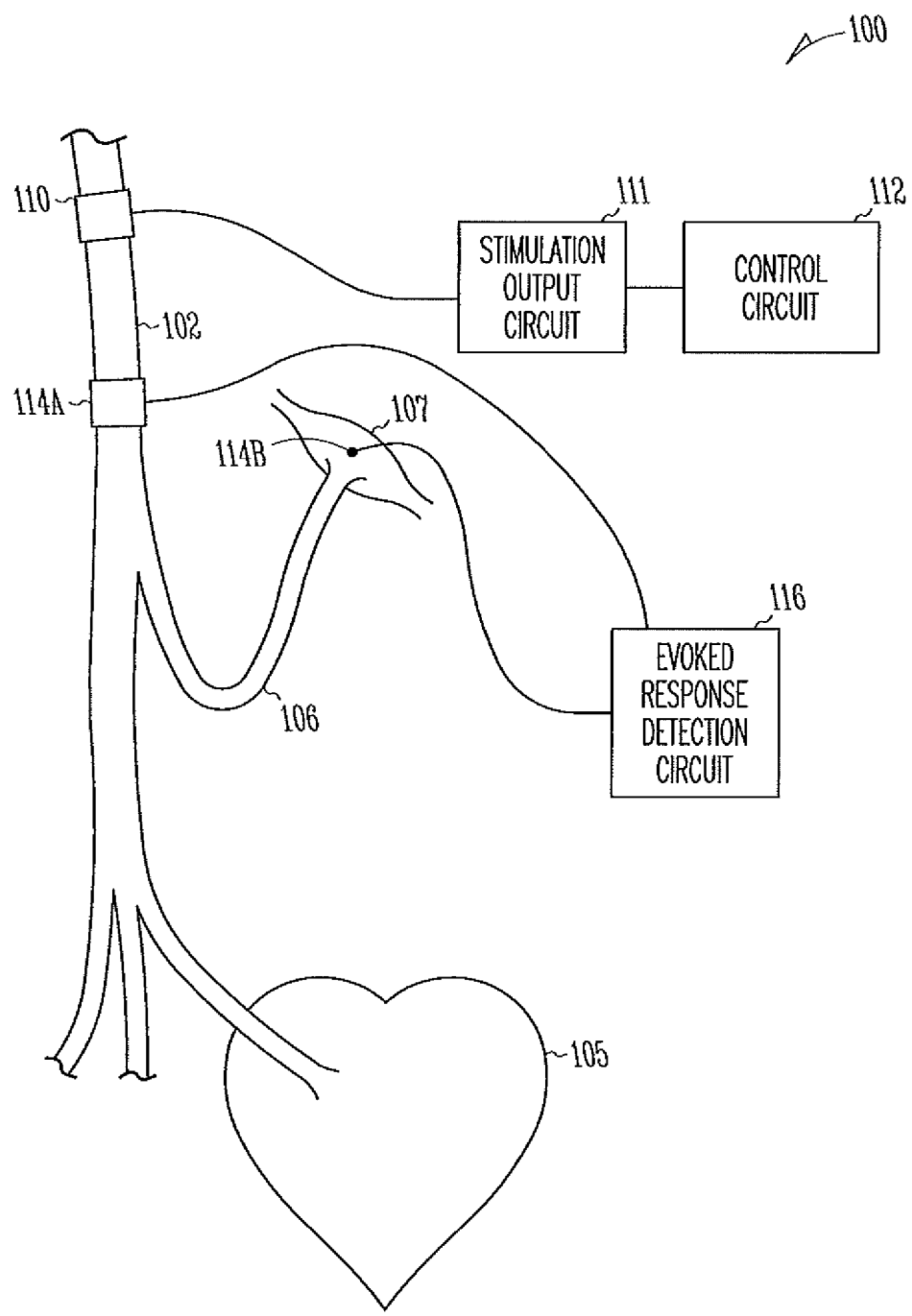
FIG. 1 is an illustration of an embodiment of a vagus nerve stimulation system and portions of an environment in which the system is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments maybe combined, or that other embodiments may be utilized and that structural, logical and electrical changes may be made without departing from the spirit and scope of the present invention. The following detailed description provides examples, and the scope of the present invention is defined by the appended claims and their legal equivalents.

It should be noted that references to "an", "one", or "various" embodiments in this disclosure are not necessarily to the same embodiment, and such references contemplate more than one embodiment.

This document discusses a method and system for delivering neurostimulation to modulate one or more target functions and detecting one or more physiological responses evoked by the neurostimulation. The detection of an evoked physiological response indicates that the nerve is captured by the stimulation. In various embodiments, each evoked physiological response is detected from a neural signal sensed from the nerve and/or from another physiological signal capable of being a surrogate of the neural signal. While a vagus nerve stimulation is specifically discussed in this document as an example, the present method and system generally applies to stimulation of various target nerves.

The vagus nerve originates in the medulla and targets multiple organs in a person's body through a complex functional innervation pattern. There are both efferent and afferent nerve fibers within the vagus nerve trunk that convey neural activities to and from visceral organs such as the esophagus, gastrointestinal tract, kidney and pancreas (abdominal branch of vagus), thoracic organs such as the heart and lungs (thoracic branch of vagus), and voluntary muscles of the neck and multiple segments of the upper airway (recurrent laryngeal nerve, RLN). In one embodiment in which vagus nerve stimulation is delivered to modulate one or more cardiovascular functions, examples of evoked responses indicating that the vagus nerve is captured include neural signals sensed from the vagus nerve and signals indicative of laryngeal activities.

Fibers of the vagus nerve include A-fibers (myelinated fibers, also referred to as A-type fibers), B-fibers (myelinated parasympathetic fibers, also referred to as B-type fibers), and C-fibers (unmyelinated fibers, also referred to as C-type fibers), as summarized in Table 1. It is believed that functions of most of the visceral and thoracic organs are modulated by vagus nerve stimulation through activation of the B-fibers, while activation of the A-fibers results in evoked laryngeal activities. As verified by experimental data, the stimulation intensity required for activating the B-fibers (stimulation threshold for B-fibers) is higher than the stimulation intensity required for activating the A-fibers (stimulation threshold for A-fibers) because the diameters of the B-fibers are smaller than the diameters of the A-fibers. The stimulation intensity required for activating the C-fibers (stimulation threshold for C-fibers) is highest because the C-fibers have the smallest diameter among those three types of fibers.

TABLE 1

Summary of Vagus Nerve Fiber Type Properties.

| | A-Fibers | B-Fibers | C-Fibers |
|---|---|---|---|
| Diameter (µm) | 5-20 | 1-3 | 0.2-2 |
| Myelinated | Yes | Yes | No |
| Conduction Velocity (m/s) | 30-120 | 3-20 | 0.3-2 |
| Per-Unit Latencies (ms/cm) | 0.08-0.3 | 0.5-3.3 | 5-33.3 |

The present method and system senses various signals indicative of the evoked neural and/or muscular responses to vagus nerve stimulation to ensure activation of the B-fibers. In various embodiments, vagus nerve stimulation is applied to modulate one or more cardiovascular functions, and one or more signals indicative of evoked neural responses of the vagus nerve and/or evoked muscular responses of the laryngeal muscles are sensed. Capture of the vagus nerve is verified by detected evoked responses, including the evoked neural and/or muscular responses. Stimulation parameters are set or adjusted to provide a stimulation intensity required for reliably activating the B-fibers.

FIG. 1 is an illustration of an embodiment of a vagus nerve stimulation system 100 and portions of an environment in which system 100 is used. System 100 includes a stimulation electrode 110, a stimulation output circuit 111, a control circuit 112, a neural sensing electrode 114A, a laryngeal activity sensor 114B, and an evoked response detection circuit 116.

FIG. 1 shows a portion of vagus nerve 102 of a patient. Vagus nerve 102 has branches including an RLN 106. Stimulation electrode 110 is electrically connected to stimulation output circuit 111 and placed on vagus nerve 102 to allow for delivery of neurostimulation pulses from stimulation output circuit 111 to modulate functions of the patient's thoracic organs, including a heart 105, and/or abdominal organs that are innervated by various branches of vagus nerve 102. In the illustrated embodiment, stimulation electrode 110 is placed on the cervical vagus nerve (the portion of vagus nerve 102 cranial to where RLN 106 branches out). RLN 106 innervates laryngeal muscles (represented by a laryngeal muscle 107), which may contract in response to the neurostimulation pulses.

Responses evoked by the neurostimulation pulses are detected. In the illustrated embodiment, neural sensing electrode 114A is placed on vagus nerve 102 to sense evoked neural responses, and laryngeal activity sensor 114B is placed in or over laryngeal muscle 107 to sense evoked muscular responses. Evoked response detection circuit 116 detects the evoked neural and/or muscular responses. In other embodiments, system 110 includes either or both of neural sensing electrode 114A and laryngeal activity sensor 114B to sense either or both of the evoked neural responses and the evoked muscular responses.

Control circuit 112 controls delivery of the neurostimulation pulses from stimulation output circuit 111. In one embodiment, control circuit 112 controls the delivery of the neurostimulation pulses using the detected evoked neural and/or muscular responses to ensure that vagus nerve 102, or one or more of its branches, is activated as intended.

In various embodiments, the circuit of system 100, including its various elements discussed in this document, is implemented using a combination of hardware and software. In various embodiments, control circuit 112 and/or evoked response detection circuit 116, including their various elements discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 2:
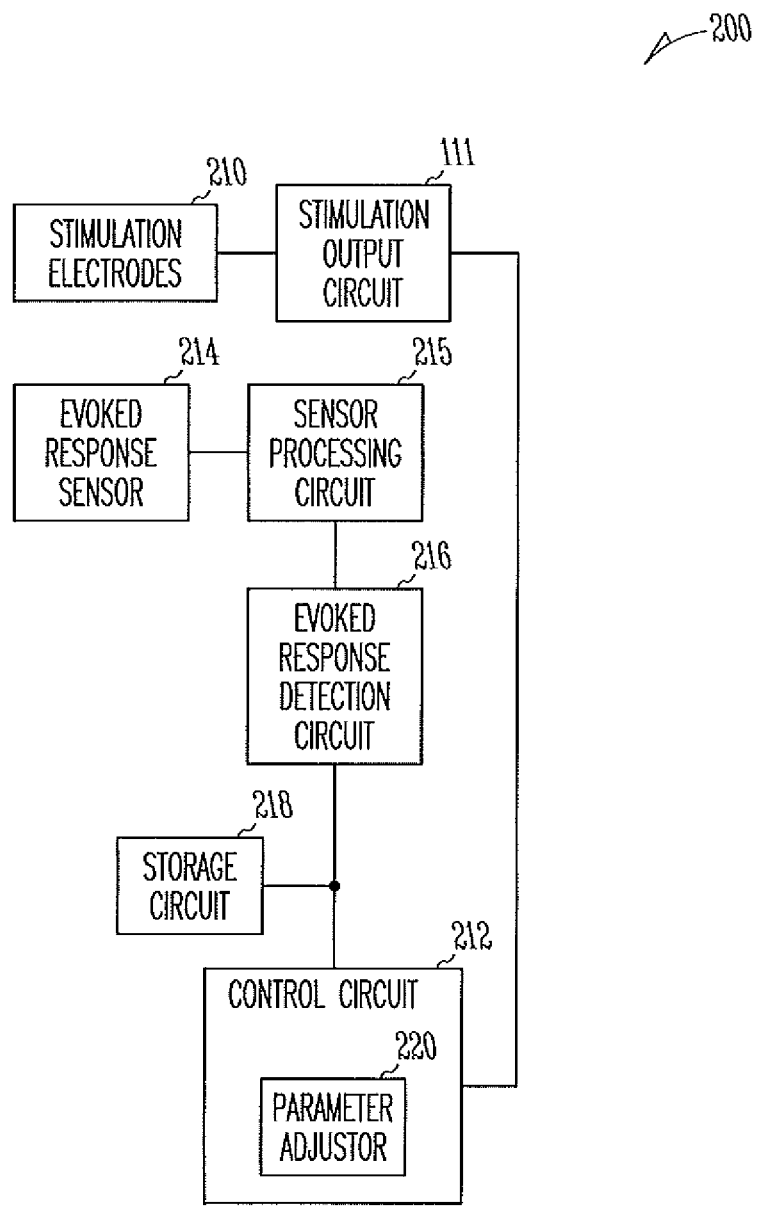
FIG. 2 is a block diagram illustrating an embodiment of a vagus nerve stimulation system providing for detection of evoked responses.

FIG. 2 is a block diagram illustrating an embodiment of a vagus nerve stimulation system 200. System 200 is an embodiment of system 100 and includes stimulation electrodes 210, stimulation output circuit 111, an evoked response sensor 214, a sensor processing circuit 215, an evoked response detection circuit 216, a control circuit 212, and a storage circuit 218.

Stimulation electrodes 210 include one or more stimulation electrodes to be placed in the patient's body in one or more locations suitable for delivering neurostimulation pulses to activate vagus nerve 102. In various embodiments, activation of vagus nerve 102 by the neurostimulation pulses includes activation of one or more portions or branches of vagus nerve 102. In one embodiment, stimulation electrodes 210 include stimulation electrode 110. In one embodiment, stimulation electrodes 210 include one or more implantable stimulation electrodes, which are incorporated into one or more implantable leads each including one or more conductors for electrically connecting the one or more stimulation electrodes to stimulation output circuit 111. In one embodiment, stimulation electrodes 210 include one or more cuff electrodes to be placed on vagus nerve 102. In one embodiment, stimulation electrodes 210 include at least a bipolar cuff electrode to be placed on vagus nerve 102. In one embodiment, stimulation electrodes 210 include a monopolar cuff electrode to be placed on vagus nerve 102 and another stimulation electrode placed in or on the patient' body. In one embodiment, stimulation electrodes 210 include at least a multi-contact electrode to be placed on or adjacent to vagus nerve 102.

Evoked response sensor 214 is to be placed in or on the patient' body in a location suitable for sensing a physiological signal indicative of evoked responses being physiologic events evoked by the neurostimulation pulses. In one embodiment, evoked response sensor 214 includes neural sensing electrode 114A to sense evoked neural responses including action potentials in vagus nerve 102 evoked by the neurostimulation pulses. The evoked neural responses include evoked A-fiber responses and evoked B-fiber responses. The evoked A-fiber responses include action potentials in the A-fibers of vagus nerve 102 evoked by the neurostimulation pulses. The evoked B-fiber responses include action potentials in the B-fibers of vagus nerve 102 evoked by the neurostimulation pulses. In one embodiment, evoked response sensor 214 includes laryngeal activity sensor 114B to sense an evoked muscular response including activities of laryngeal muscle 107 evoked by the neurostimulation pulses. In various embodiments, evoked response sensor 214 includes either or both of neural sensing electrode 114A and laryngeal activity sensor 114B. Sensor processing circuit 215 processes the physiological signal in preparation for detection of the evoked responses. Evoked response detection circuit 216 receives the processed physiological signal from sensor processing circuit 215, detects the evoked responses using the processed physiological signal, and generates one or more response signals representative of the detected evoked responses. The one or more response signals includes information about, for example, whether vagus nerve 102 is captured by the neurostimulation pulses and measured characteristics of the evoked responses.

Control circuit 212 controls the delivery of the neurostimulation pulses using a stimulation intensity that is represented by one or more stimulation parameters such as a pulse amplitude and a pulse width. The stimulation intensity is the energy in each of the neurostimulation pulses as measured by the pulse amplitude and the pulse width. Control circuit 212 includes a parameter adjustor 220 to adjust the stimulation intensity by adjusting one or more stimulation parameters. In one embodiment, parameter adjustor 220 adjusts the one or more stimulation parameters using the one or more response signals generated by evoked response detection circuit 216.

Storage circuit 218 stores the evoked responses in the form of one or more waveforms of the evoked responses and the one or more characteristic parameters of the evoked responses. In one embodiment, storage circuit 218 stores the stimulation intensity associated with detected evoked responses.

In various embodiments, the circuit of system 200, including various embodiments of its elements as illustrated in FIG. 2, is programmed to perform the various functions discussed in this document. In various embodiments, such functions allow for performance of the methods including, but not limited to, those discussed with reference to FIGS. 15, 16, and 18-20.

Figure 3:
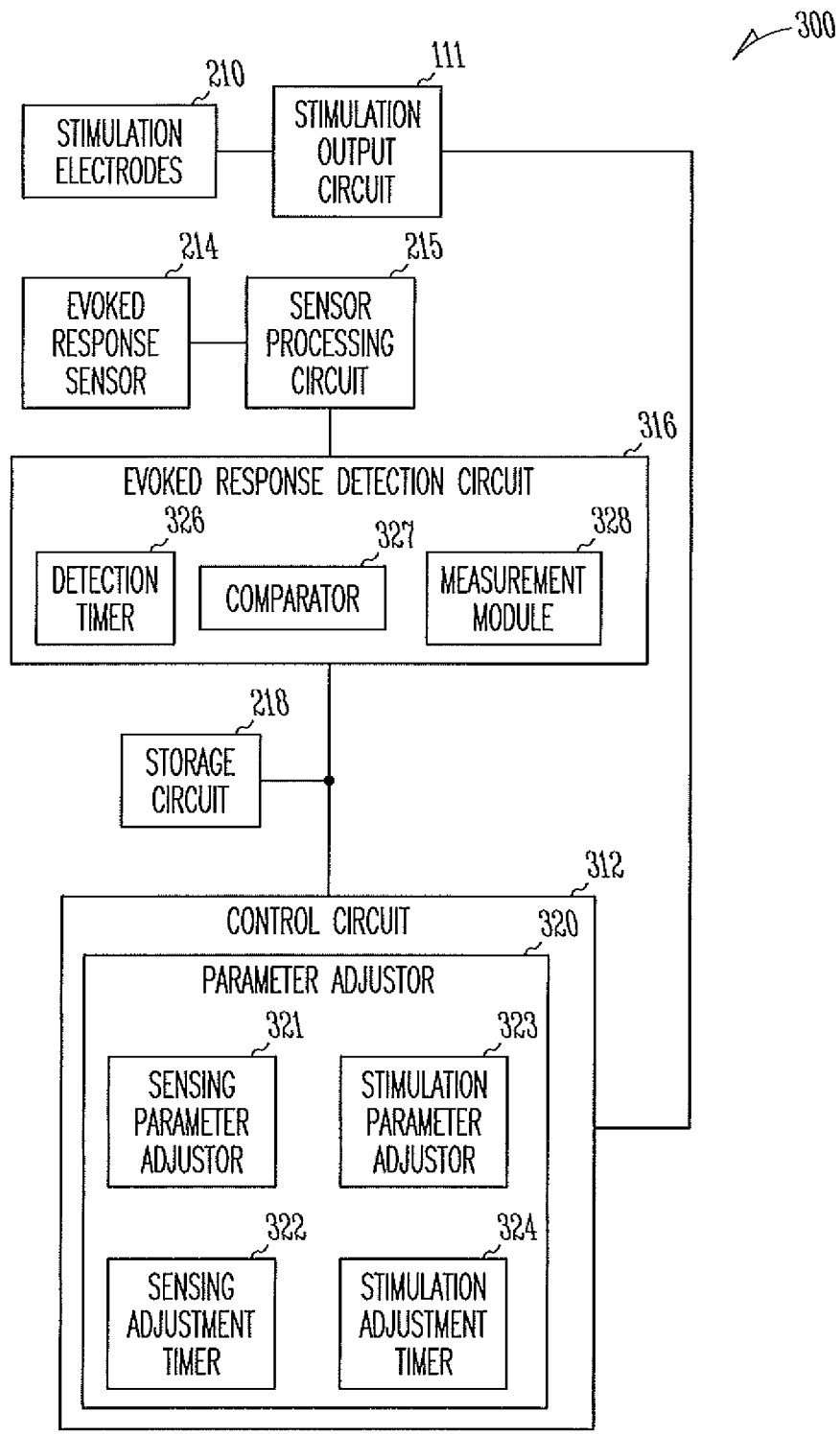
FIG. 3 is a block diagram illustrating another embodiment of the vagus nerve stimulation system of FIG. 2.

FIG. 3 is a block diagram illustrating an embodiment of a vagus nerve stimulation system 300. System 300 is an embodiment of system 100 or 200 and includes stimulation electrodes 210, stimulation output circuit 111, evoked response sensor 214, sensor processing circuit 215, an evoked response detection circuit 316, a control circuit 312, and storage circuit 218.

Evoked response detection circuit 316 is an embodiment of evoked response detection circuit 216 and detects the evoked responses using the physiological signal and generates one or more response signals representative of the detected evoked responses. Evoked response detection circuit 316 includes a detection timer 326, a comparator 327, and a measurement module 328. Detection timer 326 controls timing of detection of the evoked responses. Examples of such timing include initiation of the detection according to a specified schedule and one or more detection windows within which the evoked responses are expected to be detected. Comparator 327 detects the evoked responses by comparing the physiological signal to one or more detection thresholds. In one embodiment, comparator 327 detects the evoked responses by comparing the physiological signal to one or more detection thresholds during the one or more detection windows. Measurement module 328 measures one or more characteristic parameters of the evoked responses. Examples of the one or more characteristic parameters include amplitude of the evoked responses, width of the evoked responses, and frequency characteristics of the evoked responses. In various embodiments, the one or more characteristic parameters are each a value measured from one of the evoked responses or being an average of values measured from a plurality of the evoked responses. In various embodiments, examples of the one or more response signals include a capture verification signal declaring capture of the vagus nerve by the neurostimulation pulses and one or more signals representative of the one or more characteristic parameters of the evoked responses.

Control circuit 312 is an embodiment of control circuit 212 and controls the delivery of the neurostimulation pulses using the stimulation intensity. Control circuit 312 includes a parameter adjustor 320, which is an embodiment of parameter adjustor 220 and adjusts one or more parameters of the stimulation parameters using the one or more response signals. In the illustrated embodiment, parameter adjustor 320 includes a sensing parameter adjustor 321, a sensing adjustment timer 322, a stimulation parameter adjustor 323, and a stimulation adjustment timer 324. Sensing parameter adjustor 321 adjusts the one or more detection thresholds used by comparator 327 for detecting the evoked responses. Sensing adjustment timer 322 controls the timing of the adjustment of the one or more detection thresholds according to a specified schedule and/or in response to a user command. Stimulation parameter adjustor 323 adjusts the stimulation intensity by adjusting one or more of the stimulation parameters including either or both of the pulse amplitude and the pulse width of the neurostimulation pulses. In various embodiments, stimulation parameter adjustor 323 also adjusts other stimulation parameters such as pulse frequency, duty cycle, and stimulation duration. Stimulation adjustment timer 324 controls the timing of adjustment of the stimulation intensity according to a specified schedule and/or in response to a user command.

Figure 4:
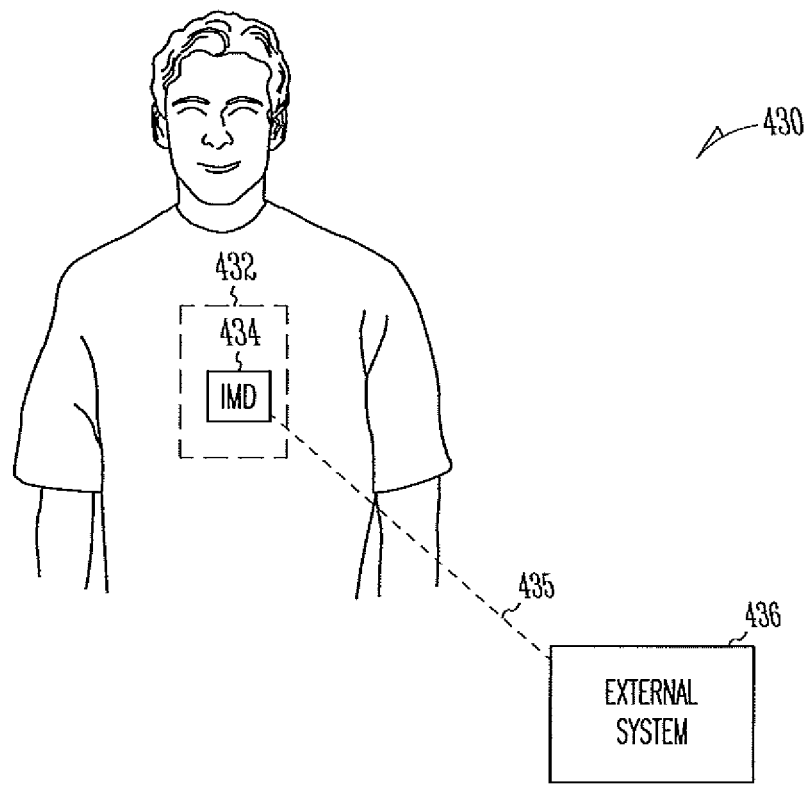
FIG. 4 is an illustration of an embodiment of an implantable system including the vagus nerve stimulation system and portions of an environment in which the implantable system is used.

FIG. 4 is an illustration of an embodiment of an implantable system 430 and portions of an environment in which implantable system 430 is used. Implantable system 430 includes system 100 including its various embodiments as discussed in this document.

System 430 includes an implantable system 432 and an external system 436. Implantable system 432 includes an implantable medical device (IMD) 434. External system 436 and IMD 434 communicate via a telemetry link 435. In various embodiments, implantable system 432 includes system 200 or system 300. In various embodiments, IMD 434 integrates a cardiac rhythm management (CRM) device with a neural sensing and stimulation device including portions of system 200 or portions of system 300. The CRM device senses cardiac electrical activities and delivers cardiac stimulation. Examples of the CRM device include pacemakers, cardioverter/defibrillators, combined pacemaker-cardioverter/defibrillators, cardiac resynchronization therapy (CRT) devices, and cardiac remodeling control therapy (RCT) devices. In various embodiments, neural activities are sensed to indicate a need for cardiac stimulation and/or to control the timing of pacing pulse deliveries. In various embodiments, cardiac activities are sensed to control the timing of neural stimulation pulse deliveries, such as to synchronize neural stimulation to cardiac cycles.

Figure 5:
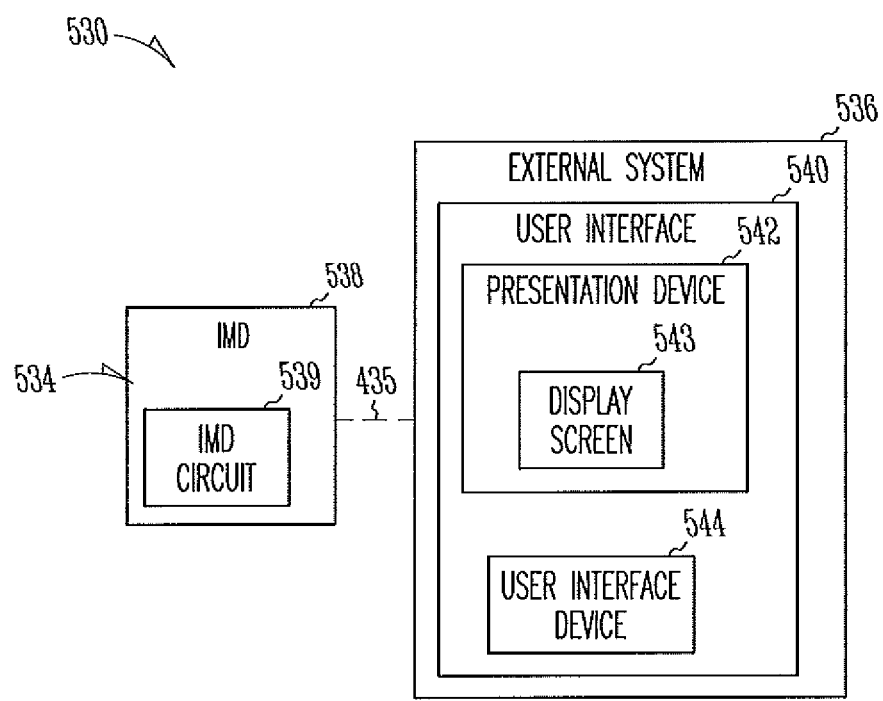
FIG. 5 is a block diagram illustrating an embodiment of the implantable system of FIG. 4

FIG. 5 is a block diagram illustrating an embodiment of an implantable system 530. Implantable system 530 is an embodiment of implantable circuit 430 and includes an IMD 534 and an external system 536.

IMD 534 is an embodiment of IMD 434 and includes an IMD circuit 539 and an implantable housing 538 encapsulating IMD circuit 539. In one embodiment, IMD circuit 539 includes at least stimulation output circuit 111 and control circuit 212 or 312. In another embodiment, IMD circuit 539 includes at least stimulation output circuit 111, sensor processing circuit 215, evoked response detection circuit 216 or 316, control circuit 212 or 312, and storage circuit 218. In various embodiments, IMD circuit 539 includes various elements of system 200 or system 300.

External system 536 is an embodiment of external system 436 and is communicatively coupled to IMD 534 via telemetry link 435. External system 536 includes a user interface 540. User interface 540 includes a presentation device 542 and a user input device 544. Presentation device 542 includes a display screen 543 to display, for example, waveforms of the detected evoked responses, the one or more response signals, the measured one or more characteristics parameters, and/or the stimulation intensity. User input device 544 receives user commands from a user such as a physician or other caregiver. Examples of the user commands include a user command for starting a delivery of the neurostimulation pulses, a user command to initiate an adjustment of the one or more detection thresholds, a user command to initiate an adjustment of the stimulation intensity, and a user command to initiate automatic capture verification as discussed in this document.

In one embodiment, external system 536 includes a programmer including user interface 540. In one embodiment, external system 536 includes a patient management system including an external device communicatively coupled to IMD 534 via telemetry link 435 and a remote device in a distant location and communicatively coupled to the external device via a communication network. The external device and/or the remote device include user interface 540.

Figure 6:
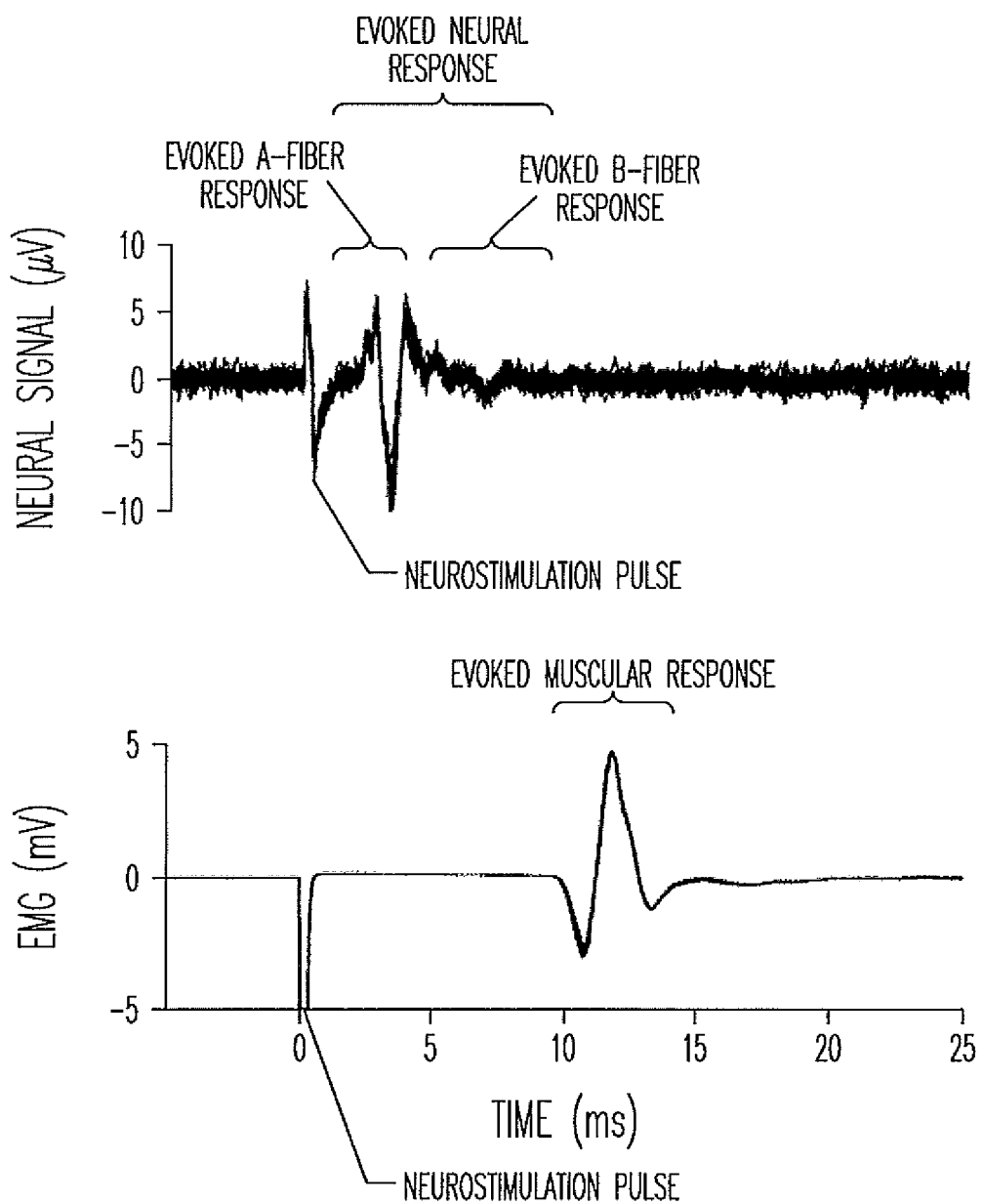
FIG. 6 is an illustration of evoked responses to a neurostimulation pulse.

FIG. 6 is an illustration of evoked responses to a neurostimlation pulse delivered to the cervical vagus nerve as seen on a neural signal recorded from the vagus nerve and an electromyographic (EMG) signal recorded from a laryngeal muscle. The neural signal includes an evoked neural response that follows the delivery of the neurostimulation pulse. The time delay between the evoked neural response and the delivery of the neurostimulation pulse is a function of the distance between the neural signal sensing site and the stimulation site. The evoked neural response includes an evoked A-fiber response and an evoked B-fiber response. As seen in FIG. 6, the evoked A-fiber response precedes the evoked B-fiber response. The EMG signal includes an evoked muscular response that follows the delivery of the neurostimulation pulse. The time delay between the evoked muscular response and the delivery of the neurostimulation pulse is a function of the distance between the EMG signal sensing site and the stimulation site. In various embodiments, the time delays are estimated using the distance between the sensing site and the stimulation site to facilitate the detection of the evoked responses.

Figure 7:
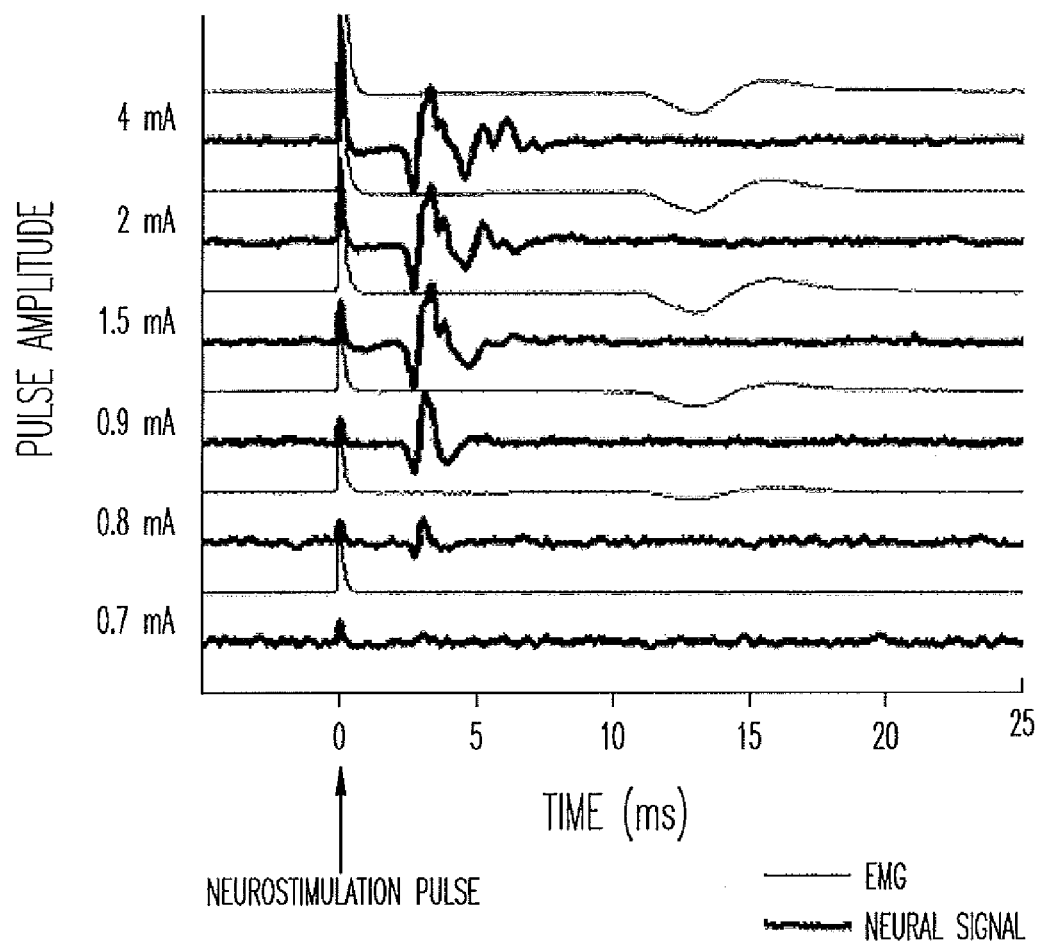
FIG. 7 is an illustration of evoked responses to neurostimulation pulses of various amplitudes.

FIG. 7 is an illustration of evoked responses to neurostimulation pulses of various intensities. Neural and EMG signals including evoked neural and muscular responses to neurostimulation pulses with different pulse amplitudes are shown. The morphology changes in the neural and EMG signals indicate that more nerve fibers are captured as the pulse amplitude increases. The minimum pulse amplitude required to evoke the A-fiber and muscular responses is lower than the minimum pulse amplitude required to evoke the B-fiber responses.

Figure 8:
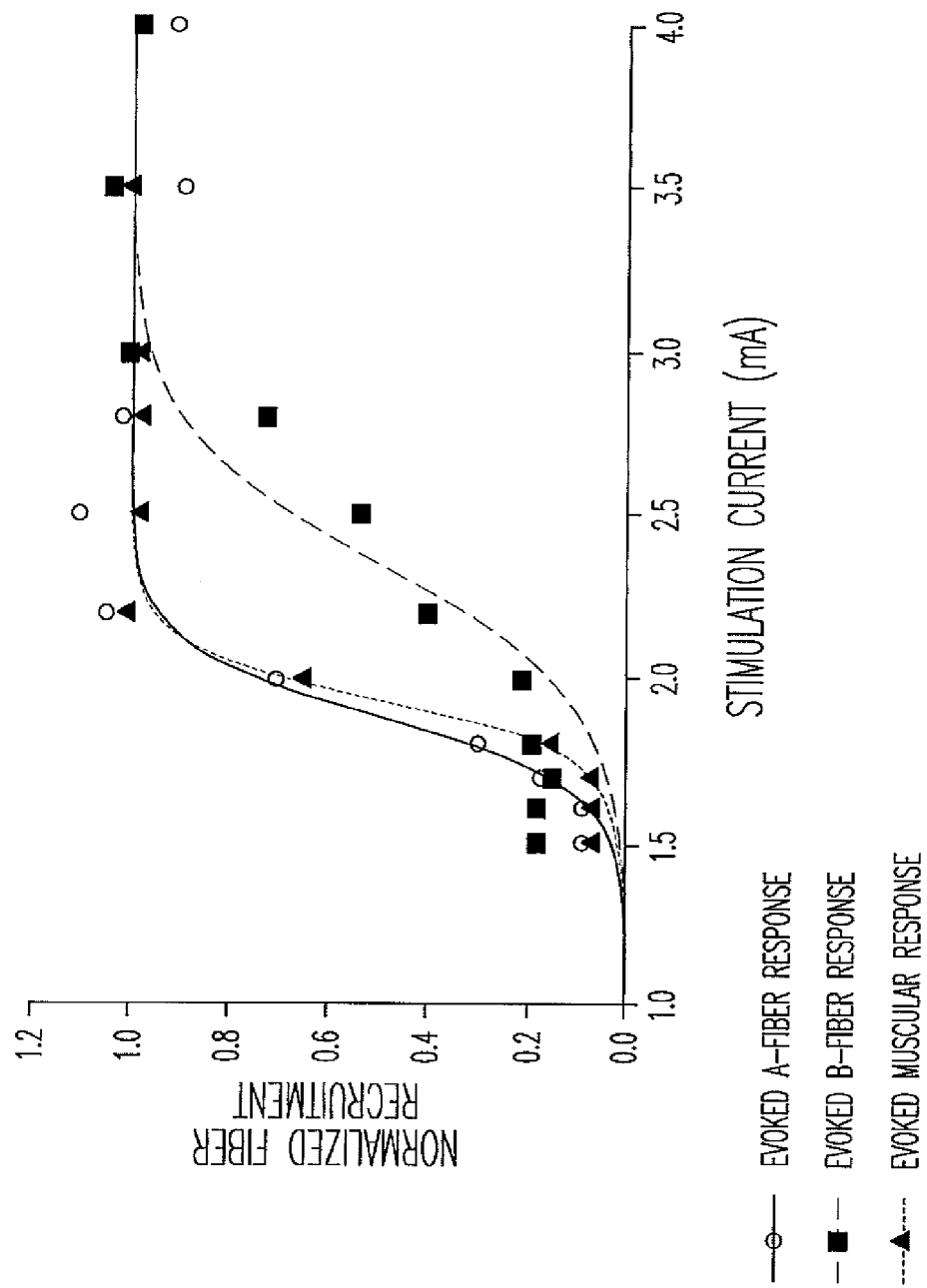
FIG. 8 is an illustration showing various stimulation thresholds.

FIG. 8 is an illustration showing recruitment curves indicative of various stimulation thresholds being the pulse amplitudes corresponding to percentage of fiber recruitment. The stimulation threshold curves show a trend consistent with what is observed from the neural and EMG signals of FIG. 7. The evoked A-fiber responses start to be detectable when the stimulation (current) amplitude is about 0.8 mA. The evoked B-fiber responses start to be detectable when the stimulation amplitude is between about 1.5 mA to 2 mA. It is believed that the A-fibers correspond to motor fibers of the vagus nerve that are primarily responsible for the activation of the laryngeal muscle, and the B-fibers correspond to part of the parasympathetic fibers of the vagus nerve that are primarily responsible for the modulation of physiologic functions including cardiovascular functions.

Figure 9:
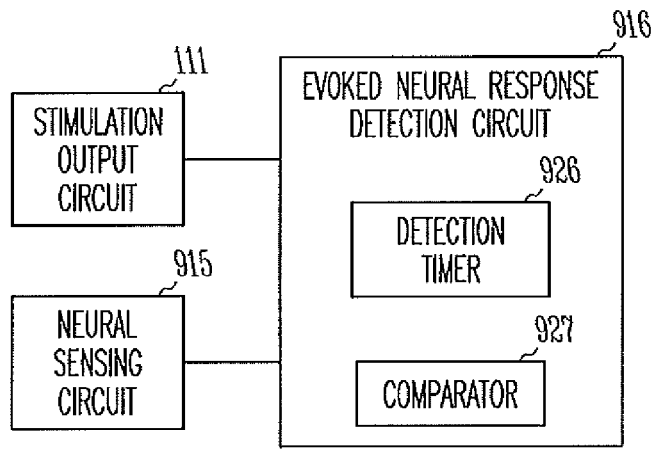
FIG. 9 is a block diagram illustrating an embodiment of a circuit for detecting evoked neural responses.
Figure 10:
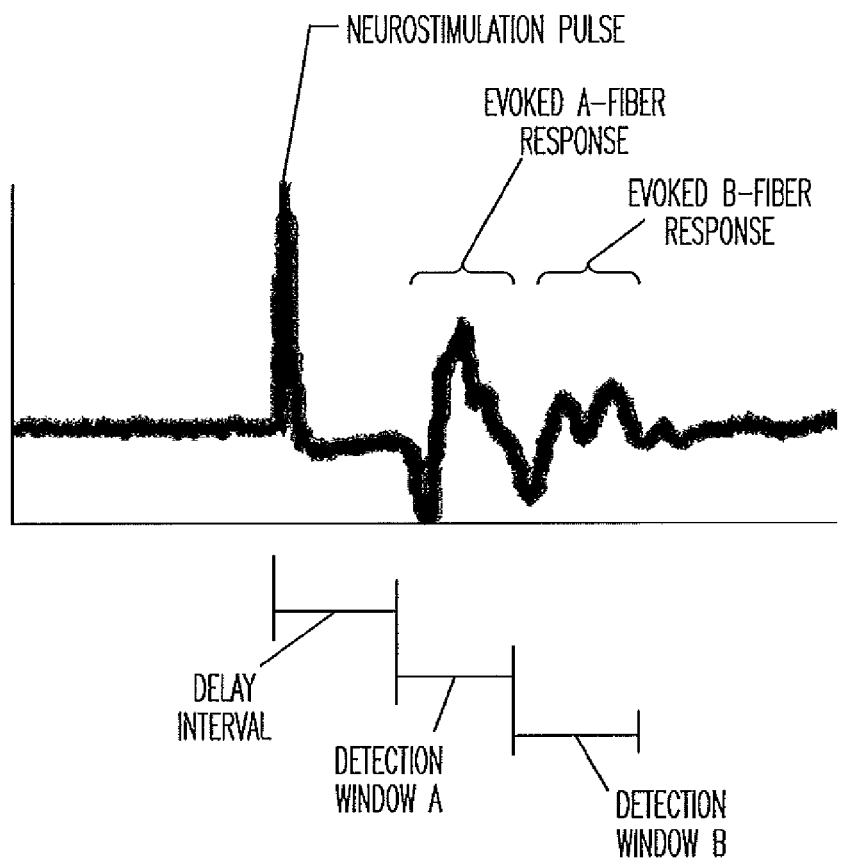
FIG. 10 is an illustration of an evoked neural response and detection windows.

FIG. 9 is a block diagram illustrating an embodiment of a circuit for detecting evoked neural responses. In one embodiment, the circuit is part of IMD circuit 539. The circuit includes stimulation output circuit 111, a neural sensing circuit 915, and an evoked neural response detection circuit 916. Stimulation output circuit 111 delivers neurostimulation pulses to the vagus nerve. Neural sensing circuit 915 is an embodiment of sensor processing circuit 215 and senses a neural signal representative of neural activities in the vagus nerve including evoked neural responses each evoked by one of the neurostimulation pulses. Evoked neural response detection circuit 916 is an embodiment of evoked response detection circuit 216 and detects the evoked neural responses using the neural signal. Evoked neural response detection circuit 916 includes a detection timer 926 and a comparator 927. Detection timer 926 times a delay interval, a detection window A, and a detection window B in response to delivery of one of the neurostimulation pulses. As illustrated in FIG. 10, the delay interval starts upon the delivery of the one of the stimulation pulses. The detection window A, which is a time window within which an evoked A-fiber response is expected, starts upon expiration of the delay interval. The detection window B, which is a time window within which an evoked B-fiber response is expected, stalls upon expiration of the detection interval A. Comparator 927 detects the evoked A-fiber response by comparing the sensed neural signal to a detection threshold A during the detection window A and detects the evoked B-fiber response by comparing the sensed neural signal to a detection threshold B during the detection window B. In another embodiment, evoked neural response detection circuit 916 includes comparator 927 but not detection timer 926. Comparator 927 detects the evoked neural responses by comparing the sensed neural signal to one or more detection thresholds.

Figure 11:
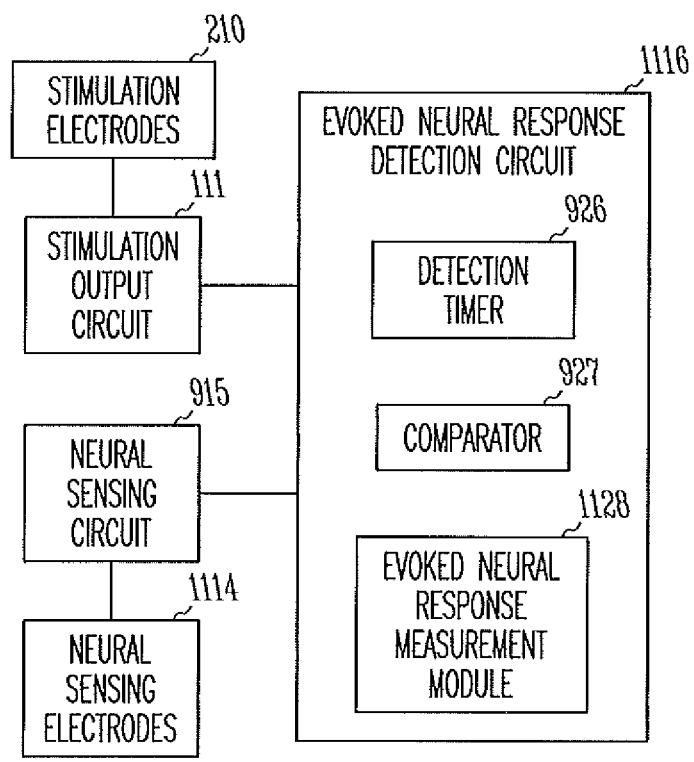
FIG. 11 is a block diagram illustrating an embodiment of a system for detecting evoked neural responses.

FIG. 11 is a block diagram illustrating an embodiment of a system for detecting evoked neural responses. The system includes stimulation electrodes 210, stimulation output circuit 111, neural sensing electrodes 1114, neural sensing circuit 915, and an evoked neural response detection circuit 1116.

Neural sensing electrodes 1114 are an embodiment of evoked response sensor 214 and are configured to be placed in the patient's body in a location suitable for sensing the neural signal representative of neural activities in the vagus nerve including evoked neural responses each evoked by one of the neurostimulation pulses. In one embodiment, neural sensing electrodes 1114 include implantable neural sensing electrodes being part of implantable system 432. In one embodiment, neural sensing electrodes 1114 include one or more cuff electrodes to be placed on the vagus nerve. Neural sensing circuit 915 is an embodiment of sensor processing circuit 215 and senses a neural signal through neural sensing electrodes 1114.

Evoked neural response detection circuit 1116 is an embodiment of evoked neural response detection circuit 916 and an embodiment of evoked response detection circuit 216 or 316 and detects the evoked neural responses using the sensed neural signal. Evoked neural response detection circuit 1116 includes at least comparator 927 and an evoked neural response measurement module 1128, and includes detection timer 926 if at least one detection window is used. In various embodiments, evoked neural response detection circuit 1116 detects the evoked neural response according to a specified schedule, such as on a periodic basis, or in response to a user command. Evoked neural response measurement module 1128 is an embodiment of measurement module 328 and measures one or more characteristic parameters of the evoked neural responses. In one embodiment, evoked neural response measurement module 1128 measures and trends the one or more characteristic parameters. Examples of the one or more characteristic parameters include amplitude of the evoked A-fiber response being the peak amplitude of the sensed neural signal during the detection window A, width of the evoked A-fiber response being the time interval during which the amplitude of the sensed neural signal exceeds the detection threshold A during the detection window A, amplitude of the evoked B-fiber response being the peak amplitude of the sensed neural signal during the detection window B, and width of the evoked B-fiber response being the time interval during which the amplitude of the sensed neural signal exceeds the detection threshold B during the detection window B.

Experimental data from an animal study indicate that the amplitude of the evoked neural response in the detection window A (i.e., the evoked A-fiber response) is in a range of approximately 5 to 20 µV, and the evoked neural response in the detection window B (i.e., the evoked B-fiber response) is in a range of approximately 1 to 6 µV. During the study, the duration of the detection window A was set to 5 ms, and the duration of the detection window B was set to 5 ms. The delay interval, or timing for initiating each of the detection window A and the detection window B depended on the distance between the stimulation site and the sensing site.

If the stimulation site and the sensing site are close to each other, it may be difficult to set the delay interval and the detection window A accurately. Consequently, it may be difficult to detect the evoked A-fiber response. However, detection of the evoke B-fiber responses is of primary interest because the B-fibers are believed to be responsible for modulating target functions of vagus nerve stimulation such as cardiovascular functions.

In one embodiment, the distance between the stimulation site and the sensing site is received from the user by user input device 544. In one embodiment, the stimulation site is where a neural stimulation electrode is placed on the vagus nerve, and the sensing site is where a neural sensing electrode is placed on the vagus nerve. Detection timer 926 determines the delay interval, the detection window A, and the detection window B each as a function of that distance. In one embodiment, the length of the delay interval, the detection window A, and the detection window B are each calibrated using the time between a non-capturing electrical neurostimulation pulse and a field effected by that pulse (not an evoked response).

Figure 12:
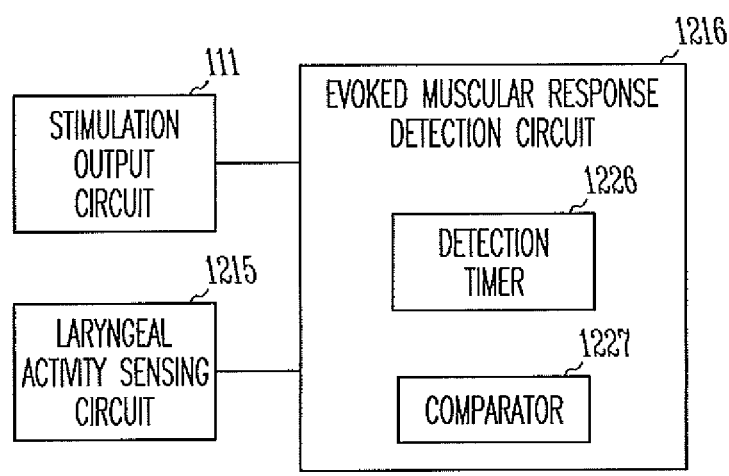
FIG. 12 is a block diagram illustrating an embodiment of a circuit for detecting evoked muscular responses.

FIG. 12 is a block diagram illustrating an embodiment of a circuit for detecting evoked muscular responses. In one embodiment, the circuit is part of IMD circuit 539. The circuit includes stimulation output circuit 111, a laryngeal activity sensing circuit 1215, and an evoked muscular response detection circuit 1216. Stimulation output circuit 111 delivers neurostimulation pulses to the vagus nerve. Laryngeal activity sensing circuit 1215 is an embodiment of sensor processing circuit 215 and senses a laryngeal signal representative of activities of the laryngeal muscle including evoked muscular responses each evoked by one of the neurostimulation pulses. Evoked muscular response detection circuit 1216 is an embodiment of evoked response detection circuit 216 and detects the evoked muscular responses using the laryngeal signal. In the illustrated embodiment, evoked neural response detection circuit 1216 includes a detection timer 1226 and a comparator 1227. Detection timer 1226 times a detection window during which the detection of an evoked muscular response is anticipated. Comparator 1227 detects the evoked muscular responses by comparing the sensed laryngeal signal to one or more detection thresholds during the detection window. In another embodiment, evoked neural response detection circuit 1216 includes comparator 1227 but not detection timer 1226. Comparator 1227 detects the evoked muscular responses by comparing the sensed laryngeal signal to one or more detection thresholds.

Figure 13:
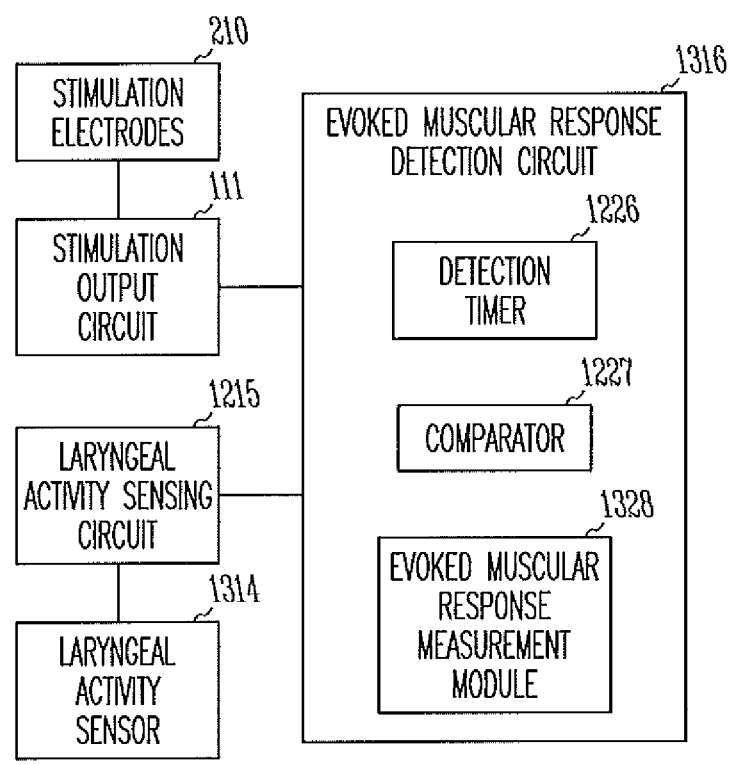
FIG. 13 is a block diagram illustrating another embodiment of a system for detecting evoked muscular responses.

FIG. 13 is a block diagram illustrating an embodiment of a system for detecting evoked muscular responses. The system includes stimulation electrodes 210, stimulation output circuit 111, a laryngeal activity sensor 1314, laryngeal activity sensing circuit 1215, and an evoked muscular response detection circuit 1316.

Laryngeal activity sensor 1314 is an embodiment of evoked response sensor 214 and is configured to be placed in or on the patient's body in a location suitable for sensing the laryngeal signal. In one embodiment, laryngeal activity sensor 1314 includes an implantable laryngeal activity sensor to be placed in the patient's body. In another embodiment, laryngeal activity sensor 1314 includes an external laryngeal activity sensor to be placed on the surface of the patient's body. Laryngeal activity sensing circuit 1215 is an embodiment of sensor processing circuit 215 and processes the signal sensed by laryngeal activity sensor 1314. Examples of the laryngeal signal, laryngeal activity sensor 1314, and laryngeal activity sensing circuit 1215 are discussed below with reference to FIG. 14.

Evoked muscular response detection circuit 1316 is an embodiment of evoked muscular response detection circuit 1216 and an embodiment of evoked response detection circuit 216 or 316, and detects the evoked muscular responses using the sensed laryngeal signal. Evoked muscular response detection circuit 1316 includes at least comparator 1227 and an evoked muscular response measurement module 1328, and includes detection timer 1226 if the detection window is used. In one embodiment, evoked muscular response detection circuit 1316 detects the evoked muscular response according to a specified schedule, such as on a periodic basis, or in response to a user command. Evoked muscular response measurement module 1328 is an embodiment of measurement module 328 and measures one or more characteristic parameters. In one embodiment, evoked muscular response measurement module 1328 measures and trends the one or more characteristic parameters. Examples of the one or more characteristic parameters include the amplitude of an evoked muscular response, the sum of multiple evoked muscular responses that follow multiple neurostimulation pulses, and the time between the delivery of a neurostimulation pulse and the detection of the evoked muscular response resulting from the delivery of that neurostimulation pulse.

Amplitude of the evoked muscular responses increases as more motor fibers (A-fibers) are captured by delivery of the neurostimulation pulses. More motor fibers are captured as the stimulation intensity increases.

It is believed that an approximately constant relationship can be identified between the stimulation threshold for capturing the A-fibers and the stimulation threshold for effectively modulating a target physiological function through capturing the B-fibers. The stimulation intensity is a minimum stimulation intensity required to evoke one or more specified physiological responses. Once an initial stimulation threshold providing for the initial evoked muscular response is determined, the stimulation intensity is set to a level that is determined by using the initial stimulation threshold and the identified approximately constant relationship. The initial evoked muscular response is the evoked muscular responses that start to become detectable as the stimulation intensity increases from a low initial level. The initial stimulation threshold is the stimulation intensity that produces the initial evoked muscular response. In one embodiment, the approximately constant relationship is quantitatively established using a patient population. The stimulation intensity for a vagus nerve stimulation therapy applied to the patient is then set using the initial stimulation threshold and the established approximately constant relationship.

Figure 14:
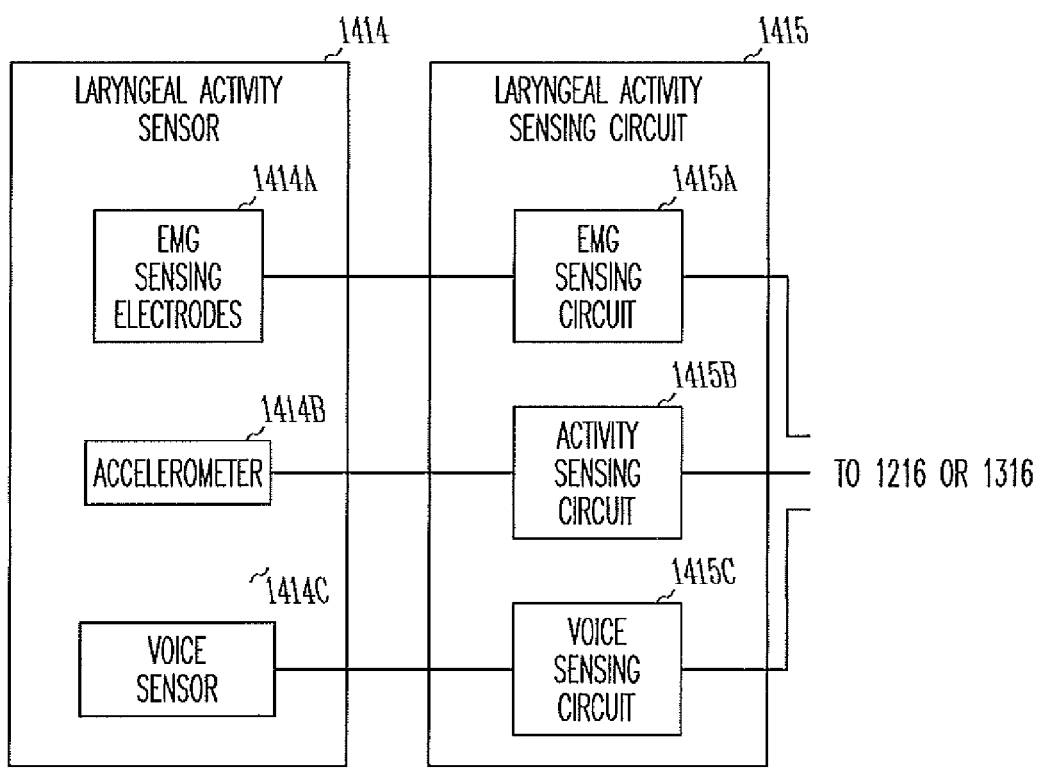
FIG. 14 is a block diagram illustrating an embodiment of a circuit for sensing various laryngeal signals.

FIG. 14 is a block diagram illustrating an embodiment of a circuit for sensing various laryngeal signals. The circuit includes a laryngeal activity sensor 1414 and a laryngeal activity sensing circuit 1415. Laryngeal activity sensor 1414 is an embodiment of laryngeal activity sensor 1314. Laryngeal activity sensing circuit 1415 is an embodiment of laryngeal activity sensing circuit 1215. In the illustrated embodiment, laryngeal activity sensor 1414 includes EMG sensing electrodes 1414A, an accelerometer 1414B, and a voice sensor 1414C, and laryngeal activity sensing circuit 1415 includes an EMG sensing circuit 1415A, an activity sensing circuit 1415B, and a voice sensing circuit 1415C. This allows for selection of a laryngeal signal by the user or the system of FIG. 13, and also allows for use of multiple laryngeal signals for the detection of the evoked muscular responses. In various embodiments, laryngeal activity sensor 1414 includes any one or more of EMG sensing electrodes 1414A, accelerometer 1414B, and voice sensor 1414C, and laryngeal activity sensing circuit 1415 includes the corresponding one or more of EMG sensing circuit 1415A, activity sensing circuit 1415B, and voice sensing circuit 1415C, depending on the laryngeal signal(s) used.

EMG sensing electrodes 1414A are configured to be placed in or on the patient's body in a location suitable for sensing an EMG signal as the laryngeal signal from laryngeal muscle 107. The EMG signal is indicative of activities of laryngeal muscle 107 including the evoked muscular response. In one embodiment, EMG sensing electrodes 1414A includes implantable EMG sensing electrodes such as intramuscular electrodes. EMG sensing circuit 1415A senses the EMG signal through EMG sensing electrodes 1414A. Evoked muscular response detection circuit 1216 or 1316 detects the evoked muscular responses using the sensed EMG signal.

Accelerometer 1414B is configured to be placed in or on the patient's body in a location suitable for sensing an acceleration signal as the laryngeal signal. The acceleration signal is indicative of activities of laryngeal muscle 107 including the evoked muscular responses. In one embodiment, accelerometer 1414B includes an implantable accelerometer. Activity sensing circuit 1415B processes the acceleration signal sensed by accelerometer 1414B. Evoked muscular response detection circuit 1216 or 1316 detects the evoked muscular responses using the processed acceleration signal.

Voice sensor 1414C is configured to be placed in or on the patient's body in a location suitable for sensing a voice signal as the laryngeal signal. In one embodiment, voice sensor 1414C includes a microphone. In one embodiment, voice sensor 1414C includes an implantable voice sensor. Vagus nerve stimulation is known to cause change in a patent's voice, such as hoarseness, by activating the laryngeal muscle. Thus, certain changes in the voice signal are indicative of activities of laryngeal muscle 107 including the evoked neuromuscular responses. Voice sensing circuit 1415C processes the voice signal sensed by voice sensor 1414C. Evoked muscular response detection circuit 1216 or 1316 detects the evoked muscular responses using the processed voice signal, such as by detecting changes in frequency characteristics of the voice signal.

Figure 15:
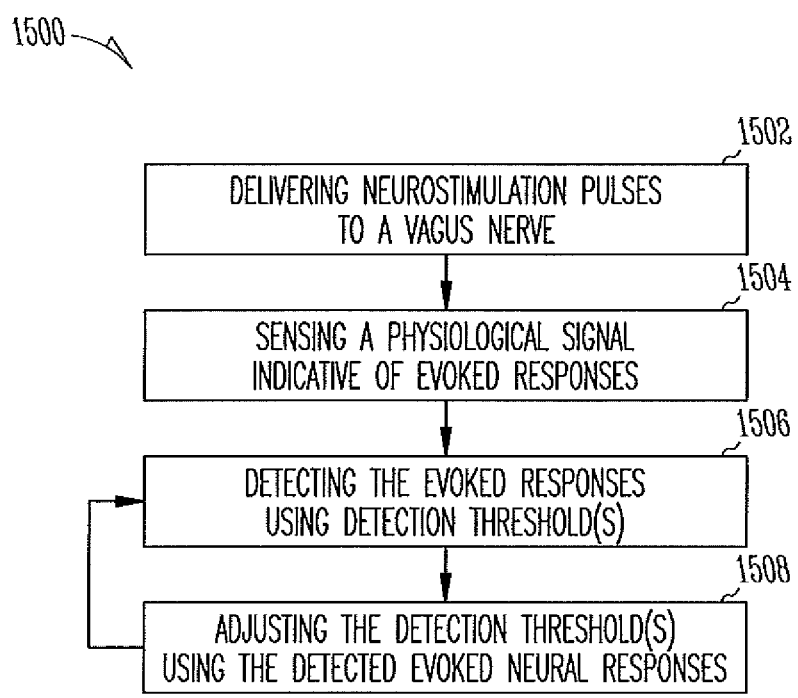
FIG. 15 is a flow chart illustrating an embodiment of a method for automatic threshold adjustment for evoked response detection during vagus nerve stimulation.

FIG. 15 is a flow chart illustrating an embodiment of a method 1500 for automatic threshold adjustment (also referred to as "Auto-Sense") for evoked response detection during vagus nerve stimulation. In various embodiments, method 1500 is performed by using system 100, including its various embodiments discussed in this document. The automatic threshold adjustment provides automatic adjustment of the one or more detection thresholds used by evoked response detection circuit 116, including its various embodiments discussed in this document. In various embodiments, evoked response detection circuit 116 is configured to perform method 1500 according to a specified schedule. In one embodiment, evoked response detection circuit 116 is configured to perform method 1500 periodically, such as monthly, weekly, daily, hourly, once each burst of the neurostimulation pulses, or once each pulse of the neurostimulation pulses.

At 1502, neurostimulation pulses are delivered to a vagus nerve. At 1504, a physiological signal is sensed. The physiological signal is indicative of evoked responses each being a physiologic event evoked by one of the neurostimulation pulses. At 1506, the evoked responses are detected by comparing the physiological signal to one or more detection thresholds. At 1508, the one or more detection thresholds are adjusted, if necessary, using the detected evoked neural responses.

In one embodiment, the physiological signal is sensed using evoked response sensor 214 and sensor processing circuit 215 at 1504. The evoked responses are detected by evoked response detection circuit 316 at 1506. The one or more detection thresholds are adjusted by sensing parameter adjustor 321. Sensing adjustment timer 322 times the performance of method 1500 according to the specified schedule or in response to a user command.

In one embodiment, the physiological signal includes a neural signal representative of neural activities in the vagus nerve including evoked neural responses each evoked by one of the neurostimulation pulses, and the evoked responses include the evoked neural responses. At 1504, the neural signal is sensed. At 1506, the evoked neural responses are detected. In one embodiment, an evoked neural response waveform representative of the evoked neural responses is detected and stored. The waveform is of one detected evoked neural response or an average of several detected evoked neural responses. In one embodiment, one or more characteristic parameters of the evoked neural responses are measured. Examples of the one or more characteristic parameters include the amplitude of the evoked A-fiber response, the width of the evoked A-fiber response, the amplitude of the evoked B-fiber response, and the width of the evoked B-fiber response as discussed above. In one embodiment, the measured one or more characteristic parameters are trended and/or stored for presentation to the user as scheduled or needed. At 1506, the one or more detection thresholds, such as the detection threshold A and the detection threshold B, are adjusted using the detected evoked neural responses. In one embodiment, the detected evoked neural responses are compared to a stored baseline response. This includes comparing the evoked neural response waveform to a stored baseline waveform and/or comparing the one or more characteristic parameters to stored one or more baseline characteristic parameters. The baseline waveform and/or the one or more baseline characteristic parameters are established for a patient during the initial system setup for the patient (such as implantation of implantable system 432), during a follow-up visit, or automatically by evoked neural response detection circuit 916 when certain criteria are met. The one or more detection thresholds are adjusted in response to the detected evoked neural responses substantially deviating from the stored baseline response. In one embodiment, the user is alerted in response to the detected evoked neural responses substantially deviating from the stored baseline response.

Figure 16:
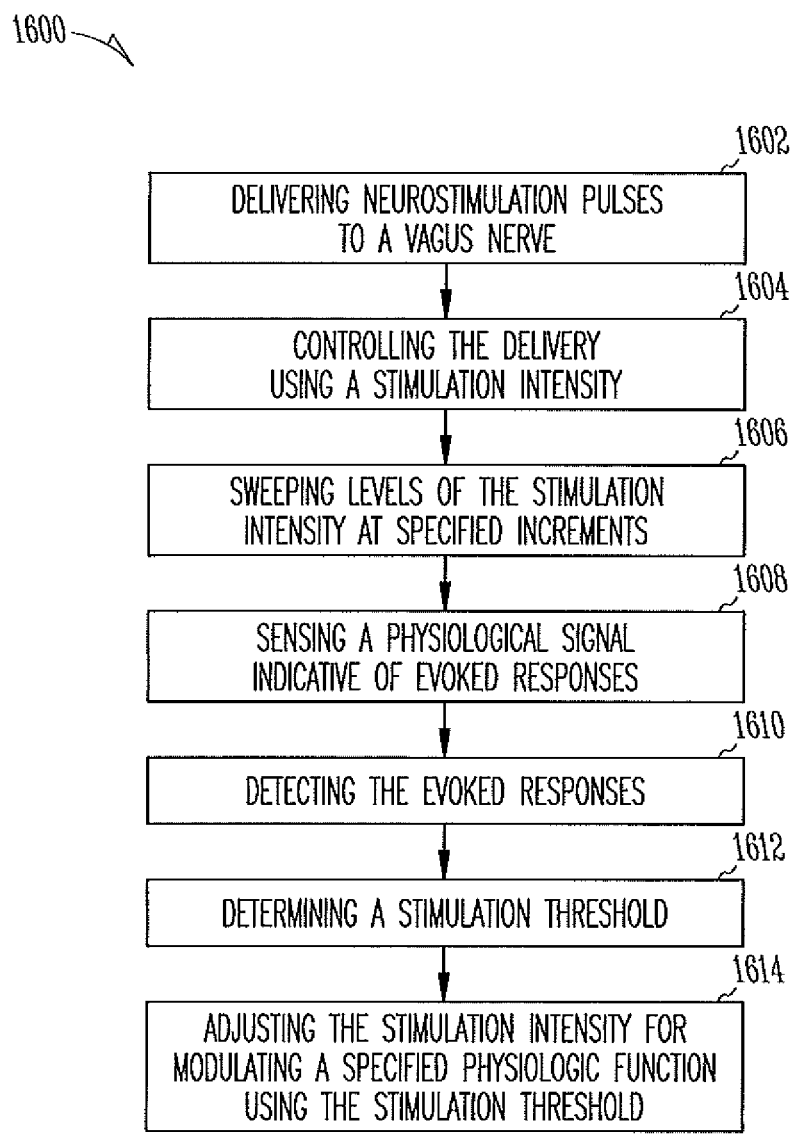
FIG. 16 is a flow chart illustrating an embodiment of a method for adjusting stimulation intensity for vagus nerve stimulation.

In one embodiment, the physiological signal includes a laryngeal signal representative of activities of the laryngeal muscle including evoked muscular responses each evoked by one of the neurostimulation pulses, and the evoked responses includes the evoked muscular responses. At 1504, the laryngeal signal is sensed. At 1506, the evoked muscular responses are detected. In one embodiment, an evoked muscular response waveform representative of the evoked muscular responses is detected and stored. The waveform is of one detected evoked muscular response or an average of several detected evoked muscular responses. In one embodiment, one or more characteristic parameters of the evoked muscular responses are measured. Examples of the one or more characteristic parameters include a maximum amplitude of the sensed laryngeal signal. In one embodiment, the measured one or more characteristic parameters are trended and/or stored for presentation to the user as scheduled or needed. At 1506, the one or more detection thresholds are adjusted using the detected evoked muscular responses. In one embodiment, the detected evoked muscular responses are compared to a stored baseline response. This includes comparing the evoked response waveform to a stored baseline waveform and/or comparing the one or more characteristic parameters to stored one or more baseline characteristic parameters. The baseline waveform and/or the one or more baseline characteristic parameters are established for a patient during the initial system setup for the patient (such as implantation of implantable system 432), during a follow-up visit, or automatically by evoked muscular response detection circuit 916 when certain criteria are met. The one or more detection thresholds are adjusted in response to the detected evoked muscular responses substantially deviating from the stored baseline response. In one embodiment, the user is alerted in response to the detected evoked muscular responses substantially deviating from the stored baseline response, FIG. 16 is a flow chart illustrating an embodiment of a method 1600 for adjusting stimulation intensity for vagus nerve stimulation. In various embodiments, method 1600 is performed by using system 100, including its various embodiments discussed in this document, At 1602, neurostimulation pulses are delivered to a vagus nerve. At 1604, the delivery of the neurostimulation pulses is controlled using a stimulation intensity. The stimulation intensity is adjustable by adjusting stimulation parameters including a pulse amplitude and a pulse width. At 1606, the stimulation intensity is swept at specified increments. At 1608 a physiological signal is sensed. The physiological signal is indicative of evoked responses each being a physiologic event evoked by one of the neurostimulation pulses. At 1610, the evoked responses are detected. At 1612, a stimulation threshold is determined. The stimulation threshold is a minimum level of the stimulation intensity for providing one or more specified characteristics of the evoked responses. At 1614, the stimulation intensity is adjusted for modulating a specified physiologic function using the stimulation threshold. In one embodiment, the physiologic function includes a cardiovascular function. In one embodiment, the stimulation threshold measured from each performance of method 1600 is trended. In various embodiments, the trend of the stimulation threshold is used to indicate pathological conditions and/or device problems. For example, a substantially increasing stimulation threshold may indicate device problems such as poor electrical connections or lead failure or pathological conditions such as nerve damages. When this happens, the user is alerted for examining the patient and the neurostimulation system. If the stimulation threshold is not determined after the stimulation intensity is swept through its maximum level, the user is also alerted because an abnormally high stimulation threshold is indicative of the device problems or pathological conditions.

In one embodiment, stimulation parameter adjustor 323 controls the sweeping of the stimulation intensity at 1606. The physiological signal is sensed using evoked response sensor 214 and sensor processing circuit 215 at 1608. The evoked responses are detected by evoked response detection circuit 316 at 1610. The stimulation threshold is determined by stimulation parameter adjustor 323 at 1612. The stimulation intensity is adjusted by stimulation parameter adjustor 323 at 1614. Stimulation adjustment timer 324 initiates and/or times the performance of method 1600 according to the specified schedule or in response to a user command.

In one embodiment, the physiological signal includes a neural signal representative of neural activities in the vagus nerve including evoked neural responses each evoked by one of the neurostimulation pulses, and the evoked responses include the evoked neural responses. At 1608, the neural signal is detected. At 1610, the evoked neural responses are detected. In one embodiment, an evoked neural response waveform representative of the evoked neural responses is detected and stored. The waveform is of one detected evoked neural response or an average of several detected evoked neural responses. At 1612, the stimulation threshold for one or more specified effects in the evoked neural response is determined. Examples of the one or more specified effects include that the amplitude of the sensed neural signal during the detection window A reaches a threshold amplitude, that the width of the evoked response detected during the detection window A reaches a threshold width, that the evoked B-fiber response is detected during the detection window B, and that a correlation between the detected evoked neural response waveform and a stored baseline waveform reaches a threshold correlation. At 1614, the stimulation intensity is adjusted for modulating a specified physiologic function, such as a cardiovascular function, using the stimulation threshold.

In one embodiment, the physiological signal includes a laryngeal signal representative of activities of the laryngeal muscle including evoked muscular responses each evoked by one of the neurostimulation pulses, and the evoked responses include the evoked muscular responses. At 1608, the laryngeal signal is detected. At 1610, the evoked muscular responses are detected. In one embodiment, an evoked muscular response waveform representative of the evoked muscular responses is detected and stored. The waveform is of one detected evoked muscular response or an average of several detected evoked muscular responses. At 1612, the stimulation threshold for one or more specified effects in the evoked muscular response is determined. Examples of the one or more specified effects include that the amplitude of the sensed laryngeal signal during a detection window reaches a threshold amplitude, that an evoked muscular response is detected during the detection window, and a correlation between the detected evoked muscular response waveform and a stored baseline waveform reaches a threshold correlation. At 1614, the stimulation intensity is adjusted for modulating a specified physiologic function, such as a cardiovascular function, using the stimulation threshold.

Figure 17:
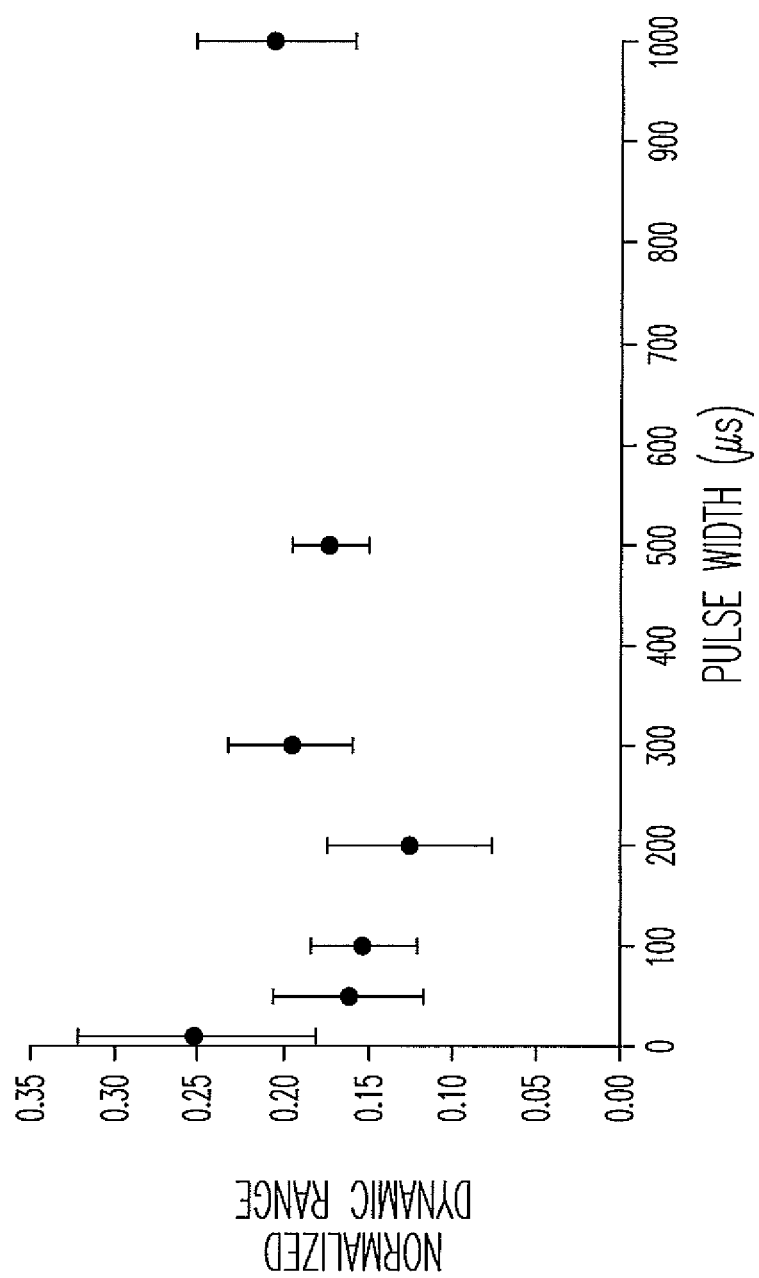
FIG. 17 is an illustration showing an example of a relationship between stimulation thresholds for two types of fibers of the vagus nerve.

In one embodiment, in which the sensed physiological signal includes the laryngeal signal, the threshold amplitude is set to a minimum amplitude of the laryngeal signal that allows for the detection of the evoked muscular responses, and the corresponding stimulation threshold is recorded as an initial stimulation threshold. The stimulation intensity is adjusted to a level calculated by using a predetermined relationship between the initial stimulation threshold and a value of the stimulation intensity associated with the specified physiological function, such as the cardiovascular function. Because it is believed that the A-fibers correspond to the motor fibers of the vagus nerve that are primarily responsible for the activation of the laryngeal muscle, and that the B-fibers correspond to part of the parasympathetic fibers of the vagus nerve that are primarily responsible for the modulation of physiologic functions including cardiovascular functions, the predetermined relationship is a relationship between the stimulation threshold for activating the A-fibers (Threshold A) and the stimulation threshold for activating the B-fibers (Threshold B). Experimental data indicate that such a relationship can be approximated by a constant. FIG. 17 is an illustration showing an example of such a relationship. The plot shows normalized dynamic ranges of a ratio of the difference between Threshold B and Threshold A to the sum of Threshold B and Threshold A, i.e., (Threshold B−Threshold A)/(Threshold B+Threshold A), for various pulse widths, where Threshold A is the stimulation threshold for recruiting about 50% of the A-fibers, and Threshold B is the stimulation threshold for recruiting about 50% of the B-fibers. Thus, the stimulation intensity is calculated by multiplying the initial stimulation threshold by the constant.

In one embodiment, method 1600 is performed by system 100 automatically. This automatic stimulation intensity adjustment (also referred to as "Auto-Threshold") provides automatic adjustment of the stimulation intensity for modulating the specified physiological function. In various embodiments, control circuit 112 and evoked response detection circuit 116, including their various embodiment as discussed in this document, are configured to perform method 1600 according to a specified schedule. In one embodiment, control circuit 112 and evoked response detection circuit 116 are configured to perform method 1600 periodically, such as monthly, weekly, daily, hourly, once each burst of the neurostimulation pulses, or once each pulse of the neurostimulation pulses. In other embodiments, adjustment of the stimulation intensity is performed by the user using system 100, as discussed below with reference to FIGS. 18 and 19.

Figure 18:
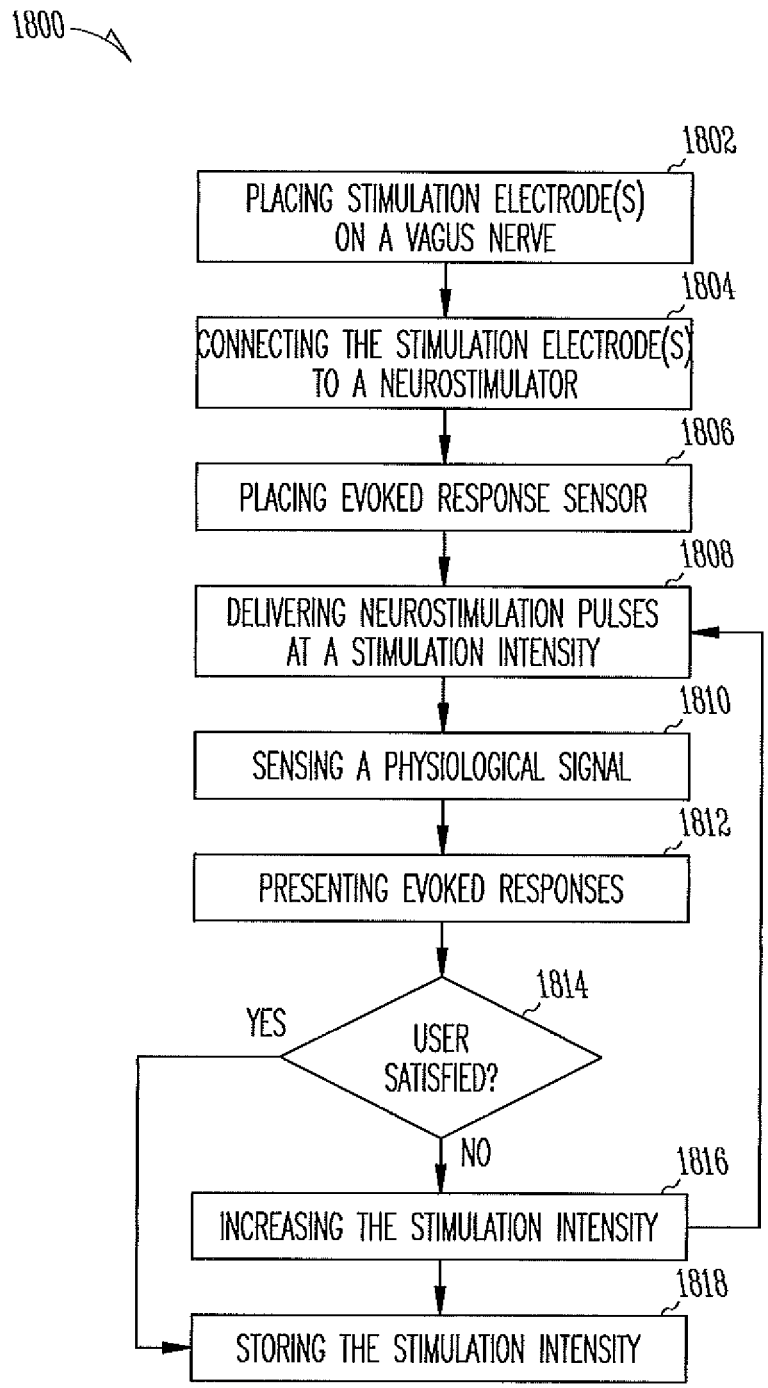
FIG. 18 is a flow chart illustrating an embodiment of a method for adjusting stimulation intensity for vagus nerve stimulation during implantation of an implantable medical device into a patient.

FIG. 18 is a flow chart illustrating an embodiment of a method 1800 for adjusting stimulation intensity for vagus nerve stimulation during implantation of an implantable medical device. In one embodiment, method 1800 is performed by the user using system 100, including its various embodiments discussed in this document.

At 1802, stimulation electrodes are placed on a vagus nerve of a patient. At 1804, the stimulation electrodes are connected to a neurostimulator including stimulation output circuit 111 and control circuit 112 for delivering neurostimulation pulses to the vagus nerve. The neurostimulator may be an external device for use during the implantable procedure or the implantable medical device intended to be implanted into the patient.

At 1806, an evoked response sensor is placed in the patient for sensing a physiological signal indicative of evoked responses each being a physiologic event evoked by one of the neurostimulation pulses. In various embodiments, this includes placing neural sensing electrodes on the vagus nerve for sensing a neural signal and/or placing a laryngeal activity sensor in a location suitable for sensing a laryngeal signal. The neural signal is representative of neural activities in the vagus nerve including evoked neural responses each evoked by one of the neurostimulation pulses. The laryngeal signal is representative of activities of the laryngeal muscle including evoked muscular responses each evoked by one of the neurostimulation pulses. In various embodiments, the evoked response sensor may be for temporary use during the implantation procedure or intended to be implanted with the implantable medical device into the patient.

At 1808, the neurostimulation pulses are delivered through the stimulation electrodes. The delivery of the neurostimulation pulses is controlled using a stimulation intensity that starts at a specified low level. The stimulation intensity is controlled by one or more stimulation parameters including the pulse amplitude and/or the pulse width. At 1810, the physiological signal is sensed.

At 1812, the evoked responses, including waveforms and measured information, are presented to the user on a display screen. When the physiological signal includes the neural signal, examples of the presented information include amplitude of the evoked neural responses, sum of a plurality of the evoked neural responses, time between the delivery of a neurostimulation pulse and the detection of the evoked neural response resulting from the delivery of that neurostimulation pulse, notation of response characteristics (e.g., "A-fiber" and "B-fiber" labels), and stimulation parameters including those controlling the stimulation intensity. When the physiological signal includes the laryngeal signal, examples of the presented information include amplitude of the evoked muscular responses, sum of a plurality of the evoked muscular responses, time between the delivery of a neurostimulation pulse and the detection of the evoked muscular response resulting from the delivery of that neurostimulation pulse, and stimulation parameters including those controlling the stimulation intensity.

At 1816, if the user is not satisfied with the evoked neural responses at 1814, the stimulation intensity is increased by increasing the pulse amplitude and/or the pulse width. If the stimulation intensity cannot be further increased, the user is alerted for examining the patient for possible pathological conditions preventing effectiveness of neurostimulation and/or the system for possible device and/or connection problems. At 1818, if the user is satisfied with the evoked neural responses associated with a level of the stimulation intensity at 1814, that level of the stimulation intensity (in terms of the pulse amplitude and the pulse width) is stored and used for the subsequent vagus nerve stimulation therapy delivered from the implantable medical device. The evoked response sensor is removed if it is for temporary use during the implantation procedure.

Figure 19:
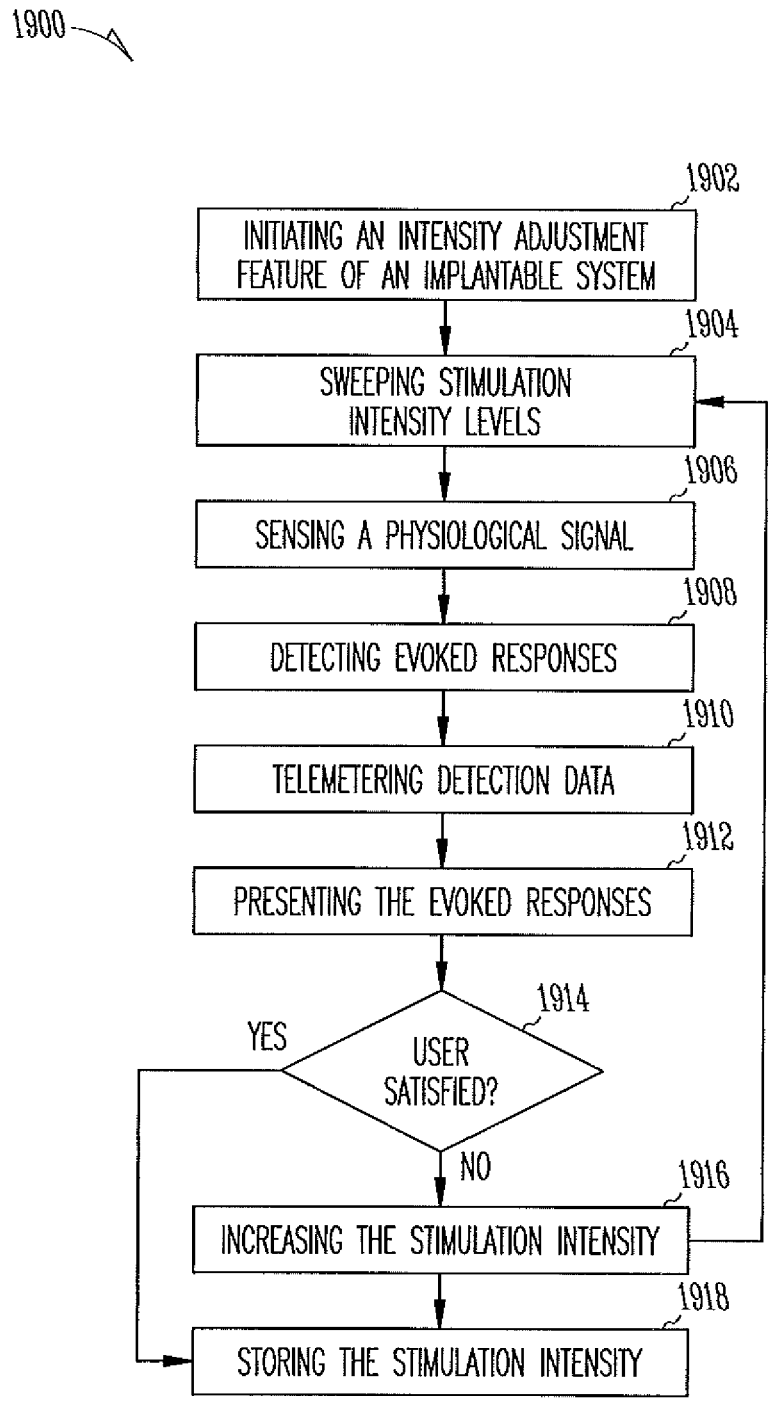
FIG. 19 is a flow chart illustrating an embodiment of a method for adjusting stimulation intensity for vagus nerve stimulation during follow-up visits by the patient using the implantable medical device.

FIG. 19 is a flow chart illustrating an embodiment of a method 1900 for adjusting stimulation intensity for vagus nerve stimulation during follow-up visits by the patient using the implantable medical device. Method 1900 is performed subsequent to method 1800. In one embodiment, method 1900 is performed by the user using system 100, including its various embodiments discussed in this document.

At 1902, an intensity adjustment feature of the implantable medical device is initiated by the user. In one embodiment, stimulation adjustment timer 423 initiates the adjustment of stimulation intensity in response to a user command entered by the user using an external system communicatively coupled to the implantable medical device. At 1904, stimulation intensity levels are swept. This includes incrementally increasing the pulse amplitude and/or the pulse width from specified low values.

At 1906, the physiological signal is sensed using the evoked response sensor that was implanted in the patient with the implantable medical device. This includes sensing of the neural signal and/or the laryngeal signal. At 1908, the evoked responses, including the evoked neural responses and/or the evoked muscular responses, are detected. At 1910, data representative of the detected evoked responses are telemetered to the external system.

At 1912, the evoked responses, including waveforms and measured information, are presented to the user on a display screen of the external system using the telemetered data. When the physiological signal includes the neural signal, examples of the presented information include amplitude of the evoked neural responses, sum of a plurality of the evoked neural responses, time between the delivery of a neurostimulation pulse and the detection of the evoked neural response resulting from the delivery of that neurostimulation pulse, notation of response characteristics (e.g., "A-fiber" and "B-fiber" labels), and stimulation parameters including those controlling the stimulation intensity. When the physiological signal includes the laryngeal signal, examples of the presented information include amplitude of the evoked muscular responses, sum of a plurality of the evoked muscular responses, time between the delivery of a neurostimulation pulse and the detection of the evoked muscular response resulting from the delivery of that neurostimulation pulse, and stimulation parameters including those controlling the stimulation intensity.

At 1916, if the user is not satisfied with the evoked neural responses at 1914, the stimulation intensity is increased by increasing the pulse amplitude and/or the pulse width. If the stimulation intensity cannot be further increased, the user is alerted for examining the patient for possible pathological conditions preventing effectiveness of neurostimulation and/or the system for possible device and/or connection problems. At 1918, if the user is satisfied with the evoked neural responses associated with a level of the stimulation intensity at 1914, that level of the stimulation intensity (in terms of the pulse amplitude and the pulse width) is stored and used for the subsequent vagus nerve stimulation therapy delivered from the implantable medical device.

Figure 20:
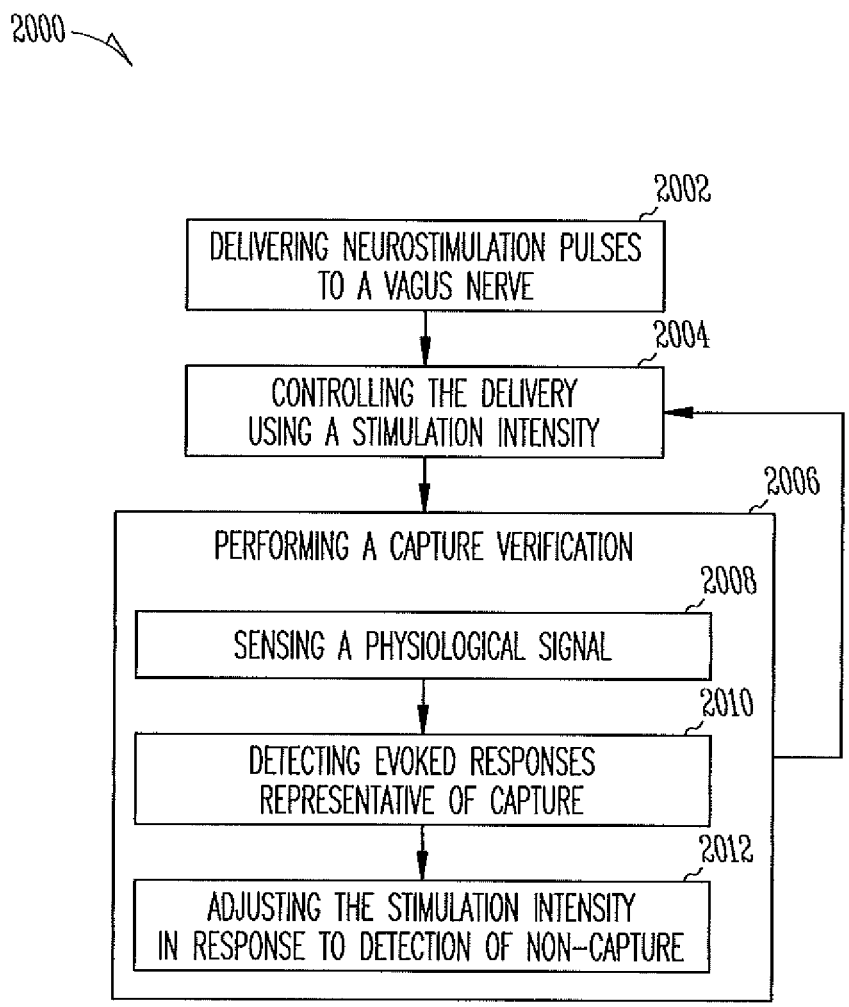
FIG. 20 is a flow chart illustrating an embodiment of a method for automatic capture verification for vagus nerve stimulation.

FIG. 20 is a flow chart illustrating an embodiment of a method 2000 for automatic capture verification (also referred to as "Auto-Capture") for vagus nerve stimulation. In various embodiments, method 2000 is performed by using system 100, including its various embodiments discussed in this document. The automatic capture verification provides automatic verification of capture of the vagus nerve by neurostimulation pulses and adjustment of the stimulation intensity. In various embodiments, control circuit 112 and evoked response detection circuit 116, including their various embodiments as discussed in this document, are configured to perform method 1600 according to a specified schedule. In one embodiment, control circuit 112 and evoked response detection circuit 116 are configured to perform method 1600 periodically, such as monthly, weekly, daily, hourly, once each burst of the neurostimulation pulses, or once each pulse of the neurostimulation pulses.

At 2002, neurostimulation pulses are delivered to a vagus nerve. At 2004, the delivery of the neurostimulation pulses is controlled using a stimulation intensity. The stimulation intensity is adjusted by adjusting stimulation parameters including a pulse amplitude and a pulse width. At 2006, a capture verification is performed. The capture verification includes sensing a physiological signal indicative of evoked responses each being a physiologic event evoked by one of the neurostimulation pulses at 2008, detecting one of the evoked responses for each pulse of the neurostimulation pulses delivered at 2010, and adjusting the stimulation intensity at 2012. The stimulation intensity is adjusted in response to specified one or more of the evoked responses not detected (i.e. non-capture) for a specified number of the neurostimulation pulses delivered. This includes adjustment of the pulse amplitude and/or the pulse width of the neurostimulation pulses. In one embodiment, the stimulation intensity is adjusted in response to an evoked response not being detected for one of the neurostimulation pulses delivered. In another embodiment, the stimulation intensity is adjusted in response to the evoked response not being detected for a specified first number of the neurostimulation pulses delivered out of a specified second number of the neurostimulation pulses delivered. In another embodiment, the stimulation intensity is adjusted in response to an evoked response not being detected for a rolling average number of the neurostimulation pulses delivered. In one embodiment, method 2000 is performed with the stimulation intensity lowered to prevent unnecessary energy delivered with the neurostimulation pulses to promote device longevity. If an unacceptable degree of loss of capture occurs when the stimulation intensity is set to about the available maximum level, the user is alerted for examining the patient for possible pathological conditions preventing effectiveness of neurostimulation and/or the system for possible device and/or connection problems.

In one embodiment, stimulation parameter adjustor 323 controls the stimulation intensity at 2004. The physiological signal is sensed using evoked response sensor 214 and sensor processing circuit 215 at 2008. The evoked responses are detected by evoked response detection circuit 316 at 2010. The stimulation intensity is adjusted by stimulation parameter adjustor 323 at 2012. Stimulation adjustment timer 324 initiates and/or times the performance of method 2000 according to the specified schedule or in response to a user command.

In one embodiment, the physiological signal includes a neural signal representative of neural activities in the vagus nerve including evoked neural responses each evoked by one of the neurostimulation pulses, and the evoked responses include the evoked neural responses. At 2008, the neural signal is sensed. At 2010, one of the evoked neural responses for each pulse of the neurostimulation pulses delivered is detected. At 2012, the stimulation intensity is adjusted in response to specified one or more of the evoked neural responses not detected (i.e. non-capture) for a specified number of the neurostimulation pulses delivered. In one embodiment, the stimulation intensity is adjusted in response to an evoked neural response not being detected for one of the neurostimulation pulses delivered. In another embodiment, the stimulation intensity is adjusted in response to the evoked neural response not being detected for a specified first number of the neurostimulation pulses delivered out of a specified second number of the neurostimulation pulses delivered. In another embodiment, the stimulation intensity is adjusted in response to an evoked neural response not being detected for a rolling average number of the neurostimulation pulses delivered.

In one embodiment, the physiological signal includes a laryngeal signal representative of activities of the laryngeal muscle including evoked muscular responses each evoked by one of the neurostimulation pulses, and the evoked responses include the evoked muscular responses. At 2008, the laryngeal signal is sensed. At 2010, one of the evoked muscular responses for each pulse of the neurostimulation pulses delivered is detected. At 2012, the stimulation intensity is adjusted in response to specified one or more of the evoked muscular responses not detected (i.e. non-capture) for a specified number of the neurostimulation pulses delivered. In one embodiment, the stimulation intensity is adjusted in response to an evoked muscular response not being detected for one of the neurostimulation pulses delivered. In another embodiment, the stimulation intensity is adjusted in response to the evoked muscular response not being detected for a specified first number of the neurostimulation pulses delivered out of a specified second number of the neurostimulation pulses delivered. In another embodiment, the stimulation intensity is adjusted in response to an evoked muscular response not being detected for a rolling average number of the neurostimulation pulses delivered.

In one embodiment, each of the automatic threshold adjustment (Auto-Sense), automatic stimulation intensity adjustment (Auto-Threshold), and automatic capture verification (Auto-Capture) is disabled or delayed if noise in the sensed physiological signal exceeds a specified threshold noise level, due to the patient's activities and speeches for example. In one embodiment, each of the automatic threshold adjustment (Auto-Sense), automatic stimulation intensity adjustment (Auto-Threshold), and automatic capture verification (Auto-Capture) is performed with various parameters such as the detection thresholds adjusted for the patient's posture and activity level.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A method for delivering neurostimulation to a body having a vagus nerve and a laryngeal muscle, the vagus nerve including A-fibers and B-fibers, the A-fibers primarily responsible for activation of the laryngeal muscle, the B-fibers primarily responsible for modulating a cardiovascular function, the method comprising:
    delivering neurostimulation pulses to the vagus nerve;
    controlling the delivery of the neurostimulation pulses using a stimulation intensity;
    sweeping levels of the stimulation intensity at specified increments;
    sensing a physiological signal indicative of evoked responses each including an activation of the A-fibers evoked by one of the neurostimulation pulses;
    detecting the evoked responses by comparing the physiological signal to one or more detection thresholds;
    determining a first stimulation threshold being a minimum level of the stimulation intensity for activating the A-fibers;
    calculating a level of the stimulation intensity for modulating the cardiovascular function by the delivery of the neurostimulation pulses using the first stimulation threshold and a predetermined relationship between the first stimulation threshold and a second stimulation threshold being a minimum level of the stimulation intensity for activating the B-fibers; and
    adjusting the stimulation intensity to the calculated level.

2. The method of claim 1, wherein sensing the physiological signal comprises sensing a neural signal representative of neural activities in the vagus nerve including evoked neural responses each including the activation of A-fibers evoked by the one of the neurostimulation pulses, detecting the evoked responses comprises detecting the evoked neural responses by comparing the neural signal to the one or more detection thresholds, and determining the first stimulation threshold comprises determining a stimulation threshold being a minimum level of the stimulation intensity for providing one or more specified characteristics of the evoked neural responses.

3. The method of claim 2, wherein determining the first stimulation threshold comprises determining a minimum level of the stimulation intensity for one or more of:
    amplitude of a response a response of the evoked neural responses reaches a threshold amplitude; and
    width of a response of the evoked neural responses reaches a threshold Width.

4. The method of claim 1, wherein sensing the physiological signal comprises sensing a laryngeal signal representative of activities of the laryngeal muscle including evoked muscular responses each including the activation of A-fibers evoked by the one of the neurostimulation pulses, detecting the evoked responses comprises detecting the evoked muscular responses by comparing the laryngeal signal to the one or more detection thresholds, and determining the first stimulation threshold comprises determining a stimulation threshold being a minimum level of the stimulation intensity for providing one or more specified characteristics of the evoked muscular responses.

5. The method of claim 4, wherein determining the first stimulation threshold comprises determining a minimum level of the stimulation intensity for the sensed laryngeal signal to exceed a amplitude.

6. The method of claim 1, comprising:
    producing an evoked response waveform representative of the detected evoked responses;
    determining a correlation between the evoked response waveform and a stored baseline waveform; and
    determining the first stimulation threshold as a minimum level of the stimulation intensity at which the correlation exceeds a threshold correlation.

7. The method of claim 1, further comprising trending the first stimulation threshold.

8. The method of claim 7, further comprising indicating pathological conditions using an outcome of the trending the first stimulation threshold.

9. The method of claim 7, further comprising indicating device problems using an outcome of the trending the first stimulation threshold.

10. The method of claim 1, further comprising determining the first stimulation threshold according to a specified schedule.

11. The method of claim 1, comprising approximating the predetermined relationship between the first stimulation threshold and the second stimulation threshold by a constant.

* * * * *